United States Patent
Raines et al.

(10) Patent No.: US 6,972,320 B2
(45) Date of Patent: Dec. 6, 2005

(54) LIGATION METHOD AND REAGENTS TO FORM AN AMIDE BOND

(75) Inventors: Ronald T. Raines, Madison, WI (US); Laura L. Kiessling, Madison, WI (US); Bradley L. Nilsson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/276,515
(22) PCT Filed: May 11, 2001
(86) PCT No.: PCT/US01/15440
§ 371 (c)(1), (2), (4) Date: Jan. 23, 2003
(87) PCT Pub. No.: WO01/87920
PCT Pub. Date: Nov. 22, 2001

(65) Prior Publication Data
US 2004/0087779 A1 May 6, 2004

Related U.S. Application Data
(60) Provisional application No. 60/203,994, filed on May 12, 2000, provisional application No. 60/209,373, filed on Jun. 5, 2000, and provisional application No. 60/255,626, filed on Dec. 13, 2000.

(51) Int. Cl.[7] .......................... C07C 231/10; C07F 9/50; C07K 1/02; C07K 1/04; C07K 1/08
(52) U.S. Cl. ....................... 530/339; 530/340; 536/124; 564/123; 568/15
(58) Field of Search ................................ 530/333, 334, 530/338, 339, 340; 564/123, 133, 134; 568/13, 15; 536/25.3, 25.32, 26.1, 26.6, 28.1, 28.6, 124

(56) References Cited

U.S. PATENT DOCUMENTS

| 4,066,684 A | * | 1/1978 | Dorman et al. ............. 530/338 |
| 5,300,278 A | | 4/1994 | Pasqualini et al. ............ 534/14 |
| 5,541,289 A | * | 7/1996 | Gilbertson ................... 530/327 |
| 5,543,389 A | | 8/1996 | Yatvin et al. .................. 514/2 |
| 6,570,040 B2 | | 5/2003 | Saxon et al. .................. 568/17 |
| 2002/0016003 A1 | | 2/2002 | Saxon et al. ................ 435/441 |
| 2003/0199084 A1 | | 10/2003 | Saxon et al. ................ 435/325 |

FOREIGN PATENT DOCUMENTS

WO   WO 01/68565   9/2001

OTHER PUBLICATIONS

Perez–Lourido et al. Diorganotin(IV) derivatives of arenephosphinothiol ligands . . . Journal of Organometallic Chemistry. 2000, vol. 595, pp. 59–65.*

Nilsson et al. Staudinger Ligation . . . Organic Letters. 2000, vol. 2, No. 13, pp. 1939–1941.*

(Continued)

Primary Examiner—Jeffrey Edwin Russel
(74) Attorney, Agent, or Firm—Greenlee, Winner and Sullivan, P.C.

(57) ABSTRACT

Methods and reagents for the formation of amide bonds between an activated carboxylic acid derivative and an azide useful in the synthesis of peptides, proteins and derivatized or labeled amino acids, peptide or proteins. The method involves the formation of a phosphinothioester which reacts with an azide resulting in amide formation. The invention provides phosphinothiol reagents which convert activated carboxylic acid derivatives to phosphinothioesters which then react with azides to form an amide bond. The methods and reagents of the invention can be used for stepwise synthesis of peptides on solid supports or for the ligation to two or more amino acids, two or more peptide or two or more protein fragments.

58 Claims, 1 Drawing Sheet

OTHER PUBLICATIONS

Saxon et al. A "Traceless" Staudinger Ligation . . . Organic Letters. 2000 vol. 2, No. 14, pp. 2141–2143.*

Afonso, C. A. M. (1998), "Studies on the Transformation of Azido–Group to N–(t–Butoxycarbonyl)amino Group via Staudinger Reaction," *Synthetic Commun.*, 28:261–276.

Ariza X. et al. (1998), "One–Pot Conversion of Azides to Boc–Protected Amines with Trimethylphosphine and Boc–ON," *Tetrahedron Lett.* 39:9101–9102.

Ariza, X. et al. (Jul. 2001), "From vacinal azido alcohols to Boc–amino alcohols or oxazolidinones, with trimethylphosphine and Boc$_2$O or CO$_2$," Tetrahedron Lett. 42:4995–4999.

Ayers, B. et al. (Feb. 1999), "Introduction of Unnatural Amino Acids into Proteins Using Expressed Protein Ligation," *Biopolymers* (including Peptide Science) 51:343–354 (published on–line Feb. 2000).

Backes, B. J.; Ellman, J. A. (Mar. 1999), "An Alkanesulfonamide 'Safety–Catch' Linker for Solid–Phase Synthesis," *J. Org. Chem.* 64: 2322–2330.

Block, E. et al. (1989), "2–Phosphino– and 2–Phosphinylbenzenethiols: New Ligand Types," *J. Am. Chem. Soc. 111*: 2327–2329.

Borgia, J.A.; Fields, G.B. (Jun. 2000), *"Chemical synthesis of proteins,"* Trends Biotechnol. 18: 243–251.

Bosch, I. et al. (1993), "Alternative Procedures for the Macrolactamisation of ω–Azido Acids," *Tetrahedron Lett.* 34:4671–4674.

Bosch, I. et al. (1995), "Epimerisation–free Peptide Formation from Carboxylic Acid Anhydrides and Azido Derivatives," *J. Chem. Soc., Chem. Commun.* pp. 91–92.

Bosch, I. et al. (1996), "On the Reaction of the Acyl Chlorides and Carboxylic Anhydrides with Phosphazenes," *J. Org. Chem.* 61:5638–5643.

Boullanger P. et al. (Feb. 2000), "Synthesis of amphiphilic glycosylamides from glycosyl azides without transient reduction to glycosylamines," *Carbohydr. Res.* 324:97–106.

Brik, A. et al. (Jun. 2000), "Protein Synthesis by SolidPhase Chemical Ligation Using a Safety Catch Linker," *J. Org. Chem.* 65(12):3829–3835.

Brisset, H. et al. (1993), "Phosphine–Borane Complexes; Direct Usein Asymmetric Catalysis," Tetrahedron Lett. 34:4523–4526.

Bruice, T. C.; Pandit, U. K. (1960), "The Effect of Geminal Substitution Ring Size and Rotamer Distribution on the Intramolecular Nucleophilic Catalysis of the Hydrolysis of Monophenyl Esters of Dibasic Acids and the Solvolysis of the Intermediate Anhydrides," *J. Am. Chem. Soc.* 82:5858–5865.

Brunel, J.M. et al. (1998), "Phosphane–boranes: synthesis, characterization and synthetic applications," Coord. Chem. Rev. 180:665–698.

Cane, D.E. et al. (1998), "Harnessing the Biosynthetic Code: Combinations, Permutations, and Mutations," *Science* 282:63–68.

Carboni, B. and Monnier, L. (Jan. 1999), "Recent Developments in the Chemistry of Amine– and Phosphine–Boranes," Tetrahedron 55:1197–1248.

Charrier, C.; Mathey, F. (1978), "La Diphenyl–Cyclopentadienylmethyl–Phospine FT SFS Complexes," (in French) *Tetrahedron Lett.* 27:2407–2410.

Cotton, G. J.; Muir, T. W. (Sep. 1999), "Peptide ligation and its application to protein engineering," *Chem. Biol.* 6:R247–R256.

Dawson, P. E. et al. (1994), "Synthesis of Proteins by Native Chemical Ligation," *Science* 266: 776–779.

Dawson, P.E.; Kent, S.B.H. (Jul. 2000), "Synthesis of Native Proteins by Chemical Ligation," *Annu. Rev. Biochem.* 69:923–960.

Dawson, P. E. et al. (1997), "Modulation of Reactivity in Native Chemical Ligation through the Use of Thiol Additives," *J. Am. Chem. Soc.* 119:4325–4329.

Drijfhout et al. (Dec. 2000), Chemical Abstracts (Columbus, Ohio, USA) No. 133:135556. Abstract of "Methods of Preparing Peptide–Carrier Conjugates," in *Fmoc Solid Phase Peptide Synthesis*), pp. 229–241.

Evans, Jr., T. C. et al. (1998), "Semisynthesis of cytotoxic proteins using a modified protein splicing element," *Protein Sci.* 7:2256–2264.

Evans, Jr., T. C.; Xu, M.–Q. (pub. on–line Feb. 2000), "Intein–Mediated Protein Ligation: Harnessing Nature's Escape Artists," *Biopolymers* 51:333–342.

Farrington, G.K. et al. (1989), "A Convenient Synthesis of Diethyl (Mercaptomethyl)Phosphate," Org. Prep. Proced. Int. 21:390–392.

Friedman, M. (Apr. 1999), "Lysinoalanine in Food and in Antimicrobial Proteins," *Adv. Exp. Med. Biol.* 459:145–159.

Garcia, J. et al. (1984), "New Synthetic "Tricks." Triphenylphosphine–Mediated Amide Formation from Carboxylic Acids and Azides," *Tetrahedron Lett.* 25:4841–4844.

Garcia, J.; Vilarrasa, J. (1986), "New Synthetic "Tricks." One–pot Preparation of N–Substituted Phthalimides from Azides and Phthalic Anhydride," *Tetrahedron Lett.* 27:639–640.

Gilbertson, S. (Aug. 2001), "High–Yielding Staudinger Ligation of Phosphinoesters and Azides to Form Amides," Chemtracts–Org. Chem. 14:524–528.

Gololobov, Yu. G.; Kasukhin, L. F. (1992), "Recent Advances in the Staudinger Reaction," *Tetrahedron 48*: 1353–1406.

Gololobov, Yu. G. et al. (1981), "Sixty Years of Staudinger Reaction," *Tetrahedron* 37: 437–472.

Holford, M.; Muir, T. W. (1998), "Adding 'splice' to protein engineering," *Structure* 15: 951–956.

Imamoto, T. et al. (1990), "Synthesis and Reactions of Phosphine–Boranes. Synthesis of New Bidentate Ligands with Homochiral Phosphine Centers via Optically Pure Phosphine–Boranes," J. Am. Chem. Soc. 112:5244–5252.

Inazu, T.; Kobayashi, K. (1993), "A New Simple Method for the Synthesis of $N^\alpha$–Fmoc–$N^\beta$–Glycosylated–L–Asparagine Derivative," *Synlett.* pp. 869–870.

Ingenito, R. et al. ( Nov. 1999), "Solid Phase Synthesis of Peptide C–Terminal Thioesters by Fmoc/t–Bu Chemistry," *J. Am. Chem. Soc.* 121:11369–11374.

Janssen, M. J. *The Chemistry of Carboxylic Acids and Esters*; Patai, S., Ed.; Interscience Publishers: New York, 1969; pp 730–736.

Jung, M. E.; Gervay, J. (1991), "gem–Dialkyl Effect in the Intramolecular Diels–Alder Reaction of 2–Furfuryl Methyl Fumarates: The Reactive Rotamer Effect, Enthalpic Basis for Acceleration, and Evidence for a Polar Transition State," *J. Am. Chem. Soc.* 113: 224–232.

Kaiser, E. T. (1989), "Synthetic Approaches to Biologically Active Peptides and Proteins Including Enzymes," *Acc. Chem. Res.* 22:47–54.

Katz, L. (1997), "Manipulation of Modular Polyketide Synthases," *Chem. Rev.* 97:2557–2575.

Keating, T.A; Walsch, C.T. (Oct. 1999), "Initiation, elongation, and termination strategies in polyketide and polypeptide antibiotic biosynthesis," *Curr. Opin.Chem. Biol.* 3:598–606.

Kemp, D. S.; Galakatos, N. G. (1986), "Peptide Synthesis by Prior Thiol Capture. 1. A Convenient Synthesis of 4–Hydroxy–6–mercaptodibenzofuran and Novel SolidPhase Synthesis of Peptide–Derived 4–(Acyloxy)–6–mercaptodibenzofurans," *J. Org. Chem.* 51:1821–1829.

Kent, S. B. (1988), "Chemical Synthesis of Peptides and Proteins," *Annu. Rev. Biochem.* 57: 957–989.

Khosla, C. (1997), "Harnessing the Biosynthetic Potential of Modular Polyketide Synthases," *Chem. Rev.* 97:2577–2590.

Kiick, K.L. et al. (Jan. 2002), "Incorporation of azides into recombinant proteins for chemoselective modification by the Staudinger ligation," Proc. Natl. Acad. Sci. USA 99:19–24.

Kochendoerfer, G. G.; Kent, S. B. H. (Dec. 1999), "Chemical protein synthesis," *Curr. Opin. Chem. Biol.* 3:665–671.

Konz, D.; Marahiel, M.A. (Feb. 1999), "How do peptide synthetases generate structural diversity?" *Chem. Biol.* 6: R39–R48.

Lamoureux, G. V.; Whitesides, G. M. (1993), "Synthesis of Dithiols as Reducing Agents for Disulfides in Neutral Aqueous Solution and Comparison of Reduction Potentials," *J. Org. Chem.* 58:633–641.

Leffler et al. (1967) "The Staudinger Reaction between Triarylphosphines and Azides. A Study of the Mechanism," J. Am. Chem. Soc. 89:5235–5246.

Lemieux et al. (1998), "Chemoselective ligation reactions with proteins, oligosaccharides and cells," Trends Biotechnol. 16:506–513.

Lemieux, G.A. et al. (Apr. 2003), "A fluorogenic dye activated by the staudinger ligation," J. Am. Chem. Soc. 125:4708–4709.

Lu, W. et al. (1996), "Comparative Total Syntheses of Turkey Ovomucoid Third Domain by Both Stepwise Solid Phase Peptide Synthesis and Native Chemical Ligation," J. Am. Chem. Soc. 118:8518–8623.

Lundberg et al. (1969) Chemical Abstracts (Columbus, Ohio, USA) No. 71:18411. Abstract of Inorganic Chemistry (1969) 8(6):1336–1340.

Lundquist, J.T., IV. and Pelletier, J.C. (Mar. 2001), "Improved Solid–Phase Peptide Synthesis Method Utilizing α–azide–Protected Amino Acids," Org. Lett. 3:781–783.

Malkinson, J. P. et al. (Aug. 2000), "Synthesis of C–Terminal Glycopeptides from Resin–Bound Glycosyl Azides via a Modified Staudinger Reaction," *J. Org. Chem.* 65:5249–5252.

Marahiel, M.A. et al. (1997), "Modular Peptide Synthetases Involved in Nonribosomal Peptide Synthesis," *Chem. Rev.* 97:2651–2673.

Marcaurelle et al. (1998), "Direct Incorporation of Unprotected Ketone Groups into Peptides During Solid–Phase Synthesis: Application to the One–Step Modification of Peptides with Two Different Biophysical Probes for FRET," Tetrahedron Lett. 39:7279–7282.

Maunier, V. et al. (1997), "Synthesis and surface–active properties of amphiphilic 6–aminocarbonyl derivatives of D–glucose," Carbohydr. Res. 299–49–57.

McCaldon, P.; Agros, P. (1988), "Oligopeptide Biases in Protein Sequences and Their Use in Predicting Protein Coding Regions in Nucleotide Sequences," *Proteins 4*: 99–122.

Meldal, M. et al. (1997), "Azido Acids in a Novel Method of Solid–Phase Peptide Synthesis," *Tetrahedron Lett.* 38:2531–2534.

Merrifield, R. B. (1984), "Solid Phase Synthesis," *Science* 232: 341–347.

Miranda, L.P. and Alewood, P.F. (pub. on–line Nov. 2000), "Challenges for Protein Chemical Synthesis in the 21$^{st}$ Century: Bridging Genomics and Proteomics," Biopolymers 55:217–226.

Mizuno, M. et al. (Jan. 1999), "A Simple Method for the Synthesis of N$^\beta$–Glycosylated–Asparagine and –Glutamine Derivatives," *Synthesis–Stuttgart*, pp. 162–165.

Mizuno, M. et al. (Jan. 1999), "Synthesis of a Glycopeptide Containing Oligosaccharides: Chemoenzymatic Synthesis of Eel Calcitonin Analogues Having Natural N–Linked Oligosaccharides," *J. Am. Chem. Soc.* 121:284–290.

Molina, P.; Vilaplana, M. J. (1994), "Iminophosphoranes: Useful Building Blocks for the Preparation of NitrogenContaining Heterocycles," *Synthesis–Stuttgart* pp. 1197–1218.

Muir, T. W. et al. (1997), "Protein Synthesis by Chemical Ligation of Unprotected Peptides in Aqueous Solution," *Methods Enzymol.* 289: 266–298.

Muir, T. W. et al. (1998), "Expressed protein ligation: A general method for protein engineering," *Proc. Natl. Acad. Sci. U.S.A.* 9:6705–6710.

Nilsson, B.L. et al. (Jun. 2000), "Staudinger Ligation: A Peptide from a Thioester and Azide," *Org. Lett.* 2:1939–1941.

Nilsson, B.L. et al. (pub. on–line Dec. 2000), "High–Yielding Staudinger Ligation of a Phosphinothioester and Azide to Form a Peptide," Org. Lett. 3:9–12.

Nilsson, B.L. et al. (May 2003), "Protein assembly by orthogonal chemical ligation methods," J. Am. Chem. Soc. 125:5468–5269.

Offer, J.; Dawson, P. E. (Jan. 2000), "N$^\alpha$–2–Mercaptobenzylamine–Assisted Chemical Ligation," *Org. Lett.* 2:23–26.

Patel, et al. (1995), Chemical Abstracts (Columbus, Ohio, USA) No. 122:133805. Abstract of J. Med. Chem. (1995) 38(3):435–442.

Perez–Lourido, P. et al. (Jan. 2000), "Diorganotin (IV) derivatives of arenephosphinothiol ligands. The crystal structure of [Ph$_2$Sn{2–(Ph$_2$P)C$_6$H$_4$S}$_2$] and [Me$_2$Sn{2–(Ph$_2$PO)–6–(Me$_3$Si)C$_6$H$_3$S}$_2$],1" J. Organomet. Chem. 595:59–65.

Perich, J.W.; and Johns, RB (1988), "Di–*tert*–butyl N,N–Diethylphosphoramidite. A New Phosphitylating Agent for the Efficient Phosphorylation of Alcohols," *Synthesis–Stuttgart* 2:142–144.

Raines, R. T. (1997), "Nature's transitory covalent bond," *Nature Struct. Biol. 4*: 424–427.

Ravinder et al. (1992), "A Novel Convenient Synthesis of Aryl Phosphines Containing Reactive Functional Groups," Synth. Comm. 22:1453–1459.

Reist, M. et al. (1995), "Racemization, Enantiomerization, Diastereomerization, and Epimerization—Their Meaning and Pharmacological Significance," Chirality 7:396–400 (Abstract only).

Romoff, T.T. and Goodman, M. (1997), "Urethane–protected N–Carboxyanhydrides (UNCAs) as unique reactants for the study of intrinsic racemization tendencies in peptide synthesis," *J. Peptide Res.* 49:281–292.

Saxon, E.; Bertozzi, C. R. (Mar. 2000), "Cell Surface Engineering by a Modified Staudinger Reaction," *Science* 267:2007–2010.

Saxon et al. (Aug. 1999), "Development of a New Chemoselective Ligation Reaction," Abstracts of Papers American Chemical Society 218:(1–2), pp. Carb 23.

Saxon, E. et al. (Jun. 2000), "A 'Traceless' Staudinger Ligation for the Chemoselective Synthesis of Amide Bonds," *Org. Lett.* 2:2141–2143.

Schneider, C. H.; de Weck, A. L. (1965), "Studies on the Direct Neutral Penicilloylation of Functional Groups Occurring on Proteins," *Biochim. Biophys. Acta 168*:27–35.

Shalev, D. E. et al. (1996), "Sequence of Reactant Combination Alters the Course of the Staudinger Reaction of Azides with Acyl Derivatives. Bimanes. 30," *J. Org. Chem.* 61:1689–1701.

Shin, Y. et al. (Dec. 1999), "Fmoc–Based Synthesis of Peptide–αThioesters: Application to the Total Chemical Synthesis of a Glycoprotein by Native Chemical Ligation," *J. Am. Chem. Soc. 121*:11684–11689.

Soellner, M.B. et al. (pub. on–line Jun. 2002), "Staudinger ligation of alpha–azido acids retains stereochemistry," *J. Org. Chem.* 67:4993–4996.

Soellner, M.B. et al. (Oct. 2003), "Site–specific protein immobilization by Staudinger ligation," J. Am. Chem. Soc. 125:11790–11791.

Staudinger, H.; Myer, J. (1919), "Über neue organische Phosphorverbindunger III. Phosphinmethylenderivative und Phosphinimine," (in German) *Helv. Chim. Acta 2*: 635–646.

Sugama, H. et al. (Jul. 2001), "P–Chirogenic Phosphine/ Sulfide Hybrid Ligands," Synthesis, (2001) 2348–2353.

Swinnen, D.; Hilvert, D. (Jul. 2000), "Facile, Fmoc–Compatible Solid–Phase Synthesis of Peptide C–Terminal Thioesters," *Org. Lett.* 2:2439–2442.

Tam, J. P.; Yu, Q.; Miao, Z. (pub. on–line Feb. 2000), "Orthogonal Ligation Strategies for Peptide and Protein," *Biopolymers 51*: 311–332.

Tam, J.P. et al (pub. on–line Dec. 2001), "Methods and Strategies of Peptide Ligation," Biopolymers 60:194–204.

Tam, J.P. et al. (1995), "Peptide synthesis using unprotected peptides through orthogonal coupling methods," *Proc. Natl. Acad. Sci. U.S.A.* 92:12485–12489.

Tam, J.P. (1988), "Synthetic peptide vaccine design: Synthesis and properties of a high–density multiple antigenic peptide system," *Proc. Natl. Acad. Sci. U.S.A.* 85:5409–5413.

Tang, Z.; Pelletier, J. C. (1998), "Preparation of amides from acids and resin bound azides: Suppression of intramolecular lactam formation," *Tetrahedron Lett. 39*:4773–4776.

Urpi, F.; Vilarrasa, J. (1986), "New Synthetic 'Tricks.' Advantages of Using Triethylphosphine in Some Phosphorus–Based Reactions," *Tetrahedron Lett.* 27:4623–4624.

Vedejs, E.; Diver, S.T. (1993), "Tributylphosphine: A Remarkable Acylation Catalyst," *J. Am. Chem. Soc. 115*: 3358–3359.

Velasco, M. D. et al. (Jun. 2000), "Isolation, Reactivity and Intramolecular Trapping of Phosphazide Intermediates in the Staudinger Reaction of Tertiary Phosphines with Azides," *Tetrahedron* 56:4079–4084.

von Dohren, H et al. (1997), "Multifunctional Peptide Synthetases," *Chem. Rev.* 97:2675–2705.

Wieland, T. et al. (1953), "Uber Peptidsynthesen. 8. Mitteilung," (In German) *Liebigs Ann. Chem. 583*:129–149.

Wilken, J.; Kent, S. B. H. (1998), "Chemical protein synthesis," *Curr. Opin. Biotechnol.* 9:412–426.

Wilt et al. (1985), "A New synthesis of Peptides from Azides and Unactivated Carboxylic Acids," J. Org. Chem. 50:2601–2603.

Woycechowsky, K. J. et al. (Dec. 1999), "A small–molecule catalyst of protein folding in vitro and in vivo," *Chem.Biol.* 6:871–879.

Zaloom, J.; Roberts, D. C. (1981), "Preparation of Azido Derivatives from Amino Acids and Peptides by Diazo Transfer," *J. Org. Chem. 46*: 5173–5176.

* cited by examiner

LIGATION METHOD AND REAGENTS TO FORM AN AMIDE BOND

CROSS-REFERENCE TO RELATED APPLICATIONS

This application is a national stage of PCT/US01/15440, filed May 11, 2001, which takes priority under 35 U.S.C. 119(e) from U.S. provisional application Ser. No. 60/203,994, filed May 12, 2000; U.S. provisional application Ser. No. 60/209,373, filed Jun. 5, 2000; and U.S. provisional application Ser. No. 60/255,626, filed Dec. 13, 2000.

STATEMENT REGARDING FEDERALLY SPONSORED RESEARCH

This invention was made with United States government support awarded by the National Institute of Health No. GM 44783. The United States government has certain rights in this invention.

BACKGROUND OF THE INVENTION

This invention is in the field of peptide chemistry, in particular relating to methods for forming amide bonds useful in the synthesis of peptides and proteins and also in the synthesis of derivatized peptides or proteins.

New methods are facilitating the total chemical synthesis of proteins. For historical references, see: Merrifield, R. B. Science 1984, 232, 341–347; Kent, S. B. Annu. Rev. Biochem. 1988, 57, 957–989; Kaiser, E. T. Acc. Chem. Res. 1989, 22, 47–54. In particular. Kent and others have developed an elegant means to stitch together two unprotected peptides in aqueous solution called "native chemical ligation." Dawson, P. E.; Muir, T. W.; Clark-Lewis, I.; Kent, S. B. Science 1994, 266, 776–779. For important precedents, see: Wieland, T.; Bokelmann, E.; Bauer, L.; Lang, H. U.; Lau, H. Liebigs Ann. Chem. 1953, 583, 129–149; Kemp, D. S.; Galakatos, N. G. J. Org. Chem. 1986, 51, 1821–1829. For reviews, see: Muir, T. W.; Dawson. P. E.; Kent, S. B. H. Methods Enzymol. 1997, 289, 266–298; Wilken, J.; Kent, S. B. H. Curr. Opin. Biotechnol. 1998, 9, 412–426; Kochendoerfer, G. G.; Kent, S. B. H. Curr. Opin. Chem. Biol. 1999, 3, 665–671; Tam, J. P.; Yu Q.; Miao, Z. Biopolymers 1999, 51, 311–332; Dawson, P. E.; Kent, S. B. H. Annu. Rev. Biochem. 2000, 69, 923–960; Borgia, J. A.; Fields, G. B. Trends Biotechnol. 2000, 18, 243–251.

In native chemical ligation the thiolate of an N-terminal cysteine residue in one peptide attacks the carbon of a C-terminal thioester in another peptide to produce, ultimately, an amide bond between the two peptides (Scheme 1). This ligation method was discovered when the reaction of ValSPh and CysOH in aqueous buffer was shown to yield the dipeptide: ValCysOH (Wieland et al., 1953).

Recently, Muir and others have expanded the utility of native chemical ligation by demonstrating that the thioester fragment can be produced readily with recombinant DNA (rDNA) techniques. Muir, T. W.; Sondhi, D.; Cole, P. A. Proc. Natl. Acad. Sci. U.S.A. 1998, 9, 6705–6710; Evans, Jr., T. C.; Benner, J.; Xu, M. -Q. Protein Sci. 1998, 7, 2256–2264; Ayers, B.; Blaschke, U. K.; Camarero, J. A.; Cotton, G. J.; Holford, M.; Muir, T. W. Biopolymers 2000, 51, 343–354. For reviews, see: Holford, M.; Muir, T. W. Structure 1998, 15, 951–956; Cotton, G. J.; Muir, T. W. Chem. Biol. 1999, 6, R247–R256; Evans, Jr., T. C.; Xu, M. Q. Biopolymers 2000, 51, 333–342. This extension of "native chemical ligation" has been designated "expressed protein ligation."

Scheme 1

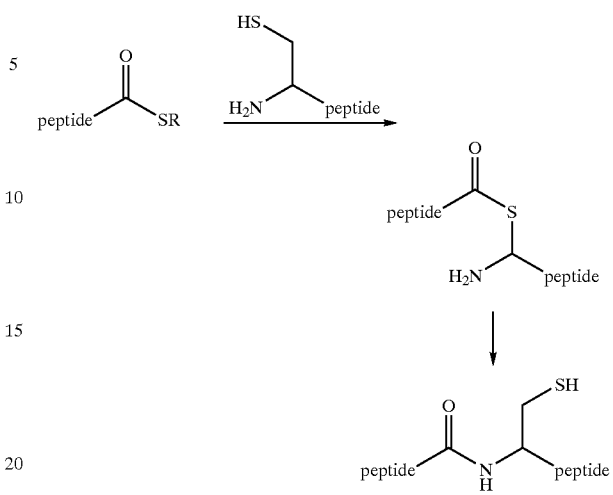

Though powerful, native chemical ligation has a serious limitation. The method has an absolute reliance on the formation of a peptide bond to a cysteine residue. Creating a linkage at a natural Xaa-Cys bond is not always possible, as cysteine comprises only 1.7% of the residues in globular proteins (McCaldon, P.; Argos, P. Proteins 1988, 4, 99–122). Modern peptide synthesis is typically limited to peptides of <50 residues (Dawson et al., 1994; Wieland et al., 1953; Kemp et al., 1986; Muir et al., 1997; Wilken et al., 1986; Kochendoerfer et al., 1999; Tam et al., 1999; Dawson et al., 2000; Borgia et al., 2000). Hence, most proteins cannot be prepared by a method that requires peptides to be coupled only at a cysteine residue.

Furthermore, installing an extra cysteine residue is often undesirable. Cysteine is by far the most reactive residue towards disulfide bonds, $O_2(g)$, and other electrophiles (Schneider, C. H.; de Weck, A. L. Biochim. Biophys. Acta 1965, 168, 27–35; Raines, R. T. Nature Struct. Biol. 1997, 4, 424–427). In addition, the sulfhydryl group of cysteine can suffer β-elimination to form dehydroalanine, which can undergo further reaction (Friedman, M. Adv. Exp. Med. Biol. 1999, 459, 145–159). Elimination of the cysteine limitation by applying a more general ligation technology would greatly expand the utility of total protein synthesis.

Offer and Dawson have recently described a peptide ligation method that does not require the presence of cysteine. (Offer, J.; Dawson, P. E. Org. Lett. 2000, 2, 23–26). In their method, a peptide bond is formed from a thioester and an o-mercaptobenzylamine. Though effective, this method necessarily leaves o-mercaptobenzylamine in the ligation product.

In the well-known Staudinger reaction a phosphine is used to reduce an azide to an amine:

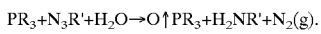

(Staudinger, H.; Meyer, J. Helv. Chim. Acta 1919, 2, 635–646. For reviews, see: Gololobov, Yu. G.; Zhmurova, I. N.; Kasukhin, L. F. Tetrahedron 1981, 37, 437–472; Gololobov, Yu. G.; Kasukhin, L. F. Tetrahedron 1992, 48, 1353–1406). The intermediate in the reaction is an iminophosphorane ($R''_3P^+$—$^-NR$), which has a nucleophilic nitrogen.

Vilarassa and others have shown that the nitrogen of the iminophosphorane can be acylated, both in intermolecular and intramolecular reactions, which have been designated "Staudinger ligations" as exemplified in reactions 1 and 2 in Scheme 2. For examples, see: Garcia, J.; Urpí, F.; Vilarrasa, J. *Tetrahedron Lett.* 1984, 25, 4841–4844; Garcia, J.; Vilarrasa, J. *Tetrahedron Lett.* 1986, 27, 639–640; Urpí, F.; Vilarrasa, J. *Tetrahedron Lett.* 1986, 27, 4623–4624; Bosch, I.; Romea, P.; Urpí, F.; Vilarrasa, J. *Tetrahedron Lett.* 1993, 34, 4671–4674; Inazu, T.; Kobayashi, K. *Synlett.* 1993, 869–870; Molina, P.; Vilaplana, M. J. *Synthesis-Stuttgart* 1994, 1197–1218; Bosch, I.; Urpí, F.; Vilarrasa, J. *J. Chem. Soc., Chem. Commun.* 1995, 91–92; Shalev, D. E.; Chiacchiera, S. M.; Radkowsky, A. E.; Kosower, E. M. *J. Org. Chem.* 1996, 61, 1689–1701; Bosch, I.; Gonzalez, A.; Urpí, F.; Vilarrasa, J. *J. Org. Chem.* 1996, 61, 5638–5643; Maunier, V.; Boullanger, P.; Lafont, D. J. *Carbohydr. Res.* 1997, 16, 231–235; Afonso, C. A. M. *Synthetic Commun.* 1998, 28, 261–276; Tang, Z.; Pelletier, J. C. *Tetrahedron Lett.* 1998, 39, 4773–4776; Ariza X.; Urpí, F.; Viladomat, C.; Vilarrasa J. *Tetrahedron Lett.* 1998, 39, 9101–9102; Mizuno, M.; Muramoto, I.; Kobayashi, K.; Yaginuma, H.; Inazu, T. *Synthesis-Stuttgart* 1999, 162–165; Mizuno, M.; Haneda, K.; Iguchi, R.; Muramoto, I.; Kawakami, T.; Aimoto, S.; Yamamoto, K.; Inazu, T. *J. Am. Chem. Soc.* 1999, 121, 284–290; Boullanger P.; Maunier, V.; Lafont, D. *Carbohydr. Res.* 2000, 324, 97–106; Velasco, M. D.; Molina, P.; Fresneda, P. M.; Sanz, M. A. *Tetrahedron* 2000, 56; 4079–4084; Malkinson, J. P.; Falconer, R. A.; Toth, I. *J. Org. Chem.* 2000, 65, 5249–5252.

Saxon and Bertozzi have reported that the phosphine can also serve as the acyl donor as illustrated in Scheme 2, reaction 3. Saxon, E.; Bertozzi, C. R. *Science* 2000, 287, 2007–2010.

Scheme 2

Vilarrasa and others (many examples in the 1980's and 1990's)

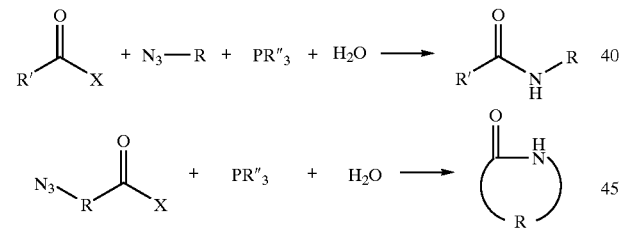

Saxon and Bertozzi (Science 2000, 287, 2007)

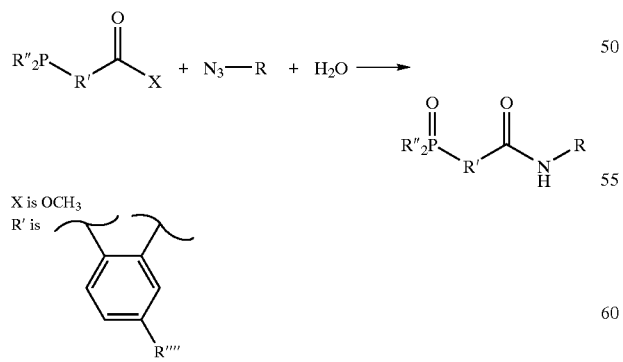

X is OCH$_3$
R' is

Recently, Saxon et al. have reported a modification of the Staudinger ligation to form an amide from an azide using a phosphine reagent. (Saxon, E.; Armstrong, J. I.; Bertozzi, C. R. *Org. Lett.* 2000, 2, 2141–2143.) The phosphine reagents:

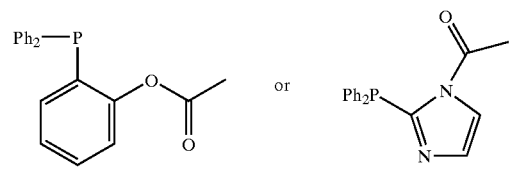

when reacted with an azidonucleoside are reported to result in the formation of an amide by acyl group transfer. The ligation is called "traceless" because no portion of the phosphine reagent other than the acyl group remains in the product. The authors also report that the reaction of the phosphinothioester:

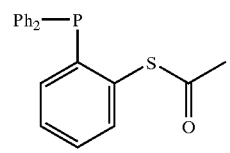

with the same azidonucleoside results initially in aza-ylide hydrolysis rather than acyl transfer. The observation of amide products after several days is characterized as the probable result of reaction of amine hydrolysis products with the thioester. The authors indicate that the phosphinothioester employed is not "amenable" to the reaction.

SUMMARY OF THE INVENTION

The invention in general provides a method and reagents for the formation of amide bonds between a phosphinothioester and an azide, as illustrated in Scheme 3. The reaction allows formation of an amide bond between a wide variety of chemical species (illustrated in Scheme 3 as $R^P$ and $R^B$). Of particular interest are those reactions in which the moieties ligated are amino acids, peptides or protein fragments. In a specific embodiment this invention provides a method and reagents for peptide ligation that eliminates the need for a cysteine residue and leaves no residual atoms in the ligated peptide product (i.e., is traceless).

Scheme 3

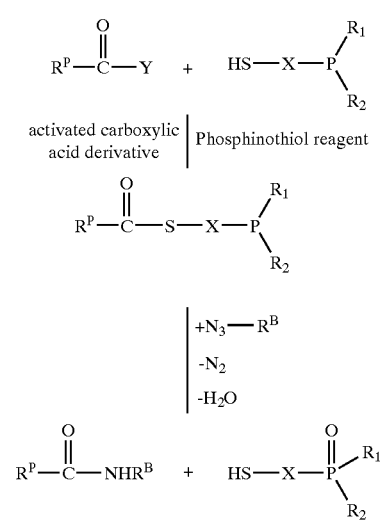

A phosphinothioester useful in this ligation can be generated in a number of ways. As illustrated in Scheme 3, an activated carboxylic acid derivative, e.g., a thioester or a N-acylsulfonamide, can be converted into a phosphinothioester. Any method known in the art for forming a phosphinothioester can in general be used. This invention provides an efficient method for generating phosphinothioesters, particularly those of amino acids, peptides and protein fragments using a phosphinothiol reagent. This reagent can be used to generate the desire phosphinothioester from activated carboxylic acid derivatives (e.g., thioesters or activated sulfamyl groups) or from a carboxylic acid by conventional coupling reactions mediated by dicyclohexylcarbodiimide or a similar coupling.

A phosphinothioester useful in the ligation reaction of this invention can also be generated from a peptide or protein fragment that is attached to a resin at its C-terminus. For example, a peptide or protein fragment can be released from a resin by reaction with a phosphinothiol reagent of this invention to generate a phosphinothioester. A peptide or protein fragment can be synthesized on an appropriate resin using known methods of solid state peptide synthesis, e.g., Fmoc-based methods. The peptide or protein fragment synthesized on the resin can then be released by reaction with a phoshinothiol to generate a phosphinothioester which then can be ligated with an azide to form an amide bond. In this aspect of the invention, any resin known in the art to be appropriate for peptide synthesis and that is compatible for reaction with a phosphinothiol to generate a phosphinothiol ester can be employed in this invention. Resins known in the art as "safety-catch" resins are of particular interest. See: Backes, B. J.; Ellman, J. A. *J. Org. Chem.* 2000, 64, 2322–2330.

The $R^P$ and $R^B$ moieties that are ligated can be any of a wide variety of chemical moieties that are compatible with the reaction conditions and which do not undergo undesired reaction with each other or with other functional groups, e.g., in $R_{1-2}$ or X in the phosphinothioester. The X moiety and $R_1$ and $R_2$ groups in Scheme 3 derive from the phosphinothiol reagent and are selected to facilitate the formation of the amide as described below.

$R^P$ and $R^B$ include moieties selected from the group consisting of aliphatic, heteroaliphatic, alicyclic, heteroalicyclic, aromatic, and heteroaromatic any of which can be substituted with one or more halides (particularly F or Cl), OH, OR, COH, COR, COOH, COOR, CONH, CONR or $N(R')_2$ groups where R, independent of other R, is an aliphatic, heteroaliphatic, alicyclic, heteroalicyclic, aromatic or heteroaromatic group and each R', independent of other R', are selected from the group hydrogen, aliphatic, heteroaliphatic, alicyclic, heteroalicyclic, aromatic or heteroaromatic groups. R and R' can, in turn, be optionally substituted as listed above. In particular, in $R^P$ and/or $R^B$ which contain aliphatic and/or alicyclic portions, one or more non-neighboring $CH_2$ groups can be replaced with O, S, CO, COO, $N(R')_2$ or CONR', where R' is as defined above. Any reactive functional group of the $R^P$ or $R^B$ group can be protected from undesired reaction by use of a protecting group (Pr).

In specific embodiments, $R^P$ and $R^B$ are amino acids, peptides, or proteins. The phospinothioester group may be formed, for example, at the carboxy terminus (C-terminus) of a peptide or protein or at an acid side group of one or more amino acids in a peptide or protein. The azido group may be formed, for example, at the amino terminus (N-terminus) of a peptide or protein or at a basic side group of one or more amino acids in a peptide or protein. The ligation method can be used to ligate two or more amino acids, two or more peptides or two or more proteins. Multiple cycles of ligation can be employed, for example, for solid state synthesis of a peptide from component amino acids. Multiple cycles of ligation can be employed to join two or more smaller peptides to form a larger peptide. The peptides joined may be obtained by solid state synthetic methods, from natural sources or by recombinant methods.

The method of this invention is particularly useful, for example, for the synthesis of peptides and proteins as illustrated in Scheme 4, where in the amino acid moieties ligated together $R^{A1}$ and $R^{A2}$, independent of other each other, are aliphatic, heteroaliphatic, alicyclic, heteroalicyclic, aromatic, or heteroaromatic any of which can be substituted as noted above. The method of this invention can be used to ligate nonnatural amino acids as well as natural amino acids enriched in particular isotopes, such as those enriched with $^{13}C$ and $^{15}N$ isotopes.

The method of this invention can also be employed to ligate one or more amino acids carrying an electrophilic side group, such as an alkyl halide or an epoxide, to each other or to incorporate one or more amino acids with electrophilic side groups into peptides and/or proteins. The method of this invention can also be employed to ligate two or more β-amino acids to each other, to ligate one or more β-amino acids to α-amino acids or incorporate one or more β-amino acids into peptides and/or proteins.

In particular, $R^{A1}$ and $R^{A2}$ groups include any side group of an acidic, basic, nonpolar or polar amino acid. $R^{A1}$ and $R^{A2}$ include side chains or side groups of the 20 common α-amino acids, as well as, side groups of uncommon amino acids (e.g., homoserine) found in proteins and side groups of other biologically active amino acids (e.g., ornithine or citrulline). The product containing the amide bond in the reaction illustrated in Scheme 4 is a dipeptide.

Scheme 4

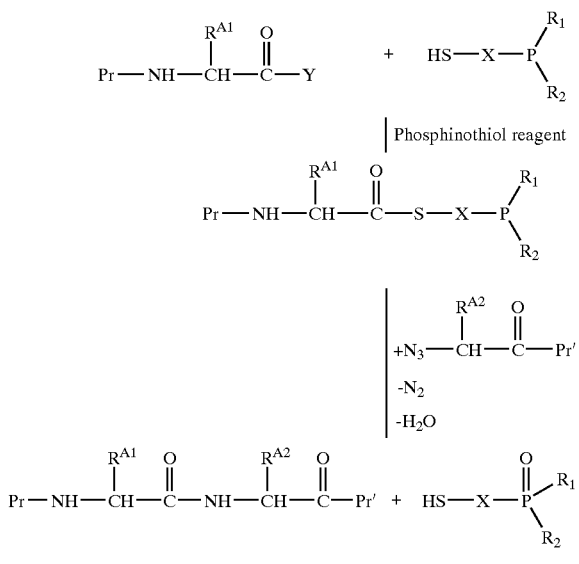

Additional amino acids can be joined to the peptide product illustrated in Scheme 4 by (1) addition of an azido group at the N-terminus of the peptide and reacting the azido-peptide with another phosphinothioester of an amino acid (or of a peptide) or (2) by formation of a phosphinothioester at the C-terminus of the peptide and subsequent reaction of the phosphinothioester formed with an azido acid (or an N-terminal azido peptide). A phosphinothiol reagent of this invention can be used to generate the phosphinothioester. These steps are illustrated in Scheme 5. Repeated cycles of steps 1 and/or 2 can be used to generate longer peptides.

Scheme 5

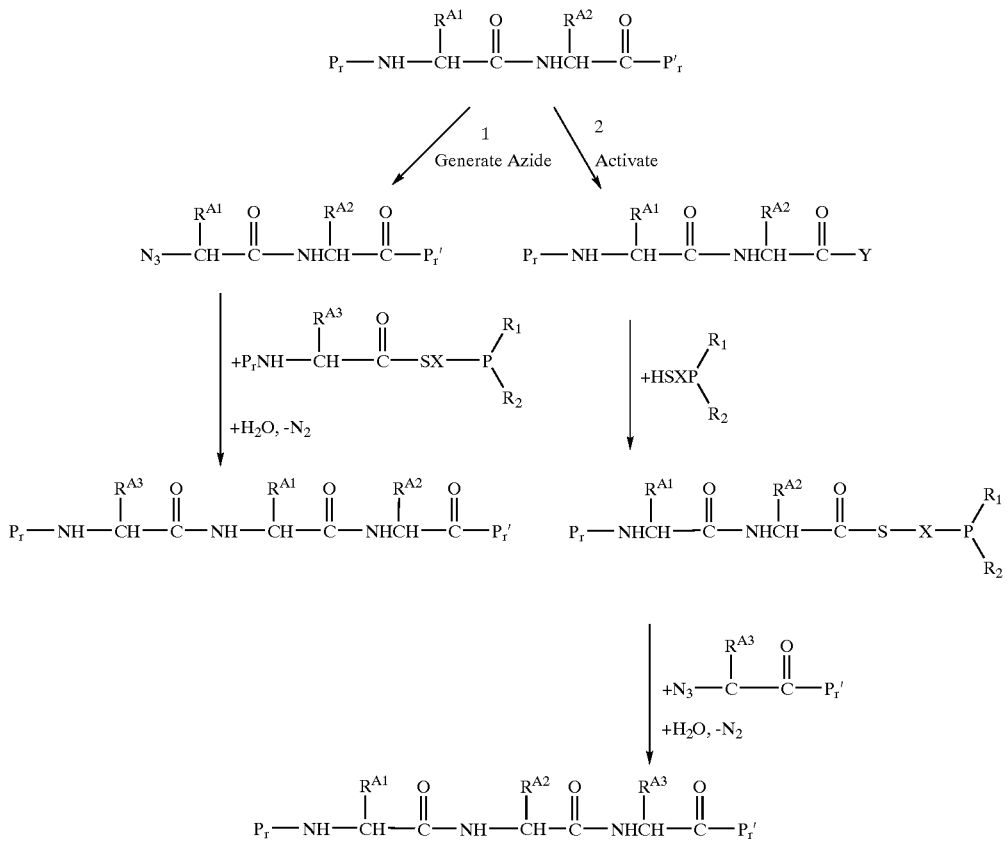

The method of this invention can also be employed for the synthesis of larger peptides or proteins by ligating two or more smaller peptides (typically less than 50 amino acids long) or to the synthesis of a protein by ligation of two or more peptides or proteins. In this method, the two or more peptides or proteins (which may be the same or different) to be ligated can be synthesized by conventional solid phase methods, e.g., Fmoc-based methods, obtained from natural sources, or obtained by recombinant methods. One of the two peptides or proteins to be ligated is derivatized with a phosphinothioester group at its C-terminus and the N-terminus is protected with an appropriate protecting group. Ihe other of the two peptides or proteins to be ligated is derivatized with an azido acid group at its N-terminus and is protected with an appropriate protecting group. The peptide phosphinothioester can, for example, be generated from a resin bound peptide or protein fragment using a phosphinothiol reagent of this invention or by reaction (transesterification or coupling reaction) of a peptide thioester with the phosphinothiol reagent. The peptide phosphinothioester is then reacted with the azido peptide accompanied by hydrolysis and loss of nitrogen to generate an amide bond ligating the two peptides. The ligation reaction may be conducted in an organic solvent containing sufficient water to facilitate hydrolysis and amide generation, e.g., a mixture of THF and water. Alternatively, the reaction of the phosphinothioester and the azide can be initiated in an organic solvent (in which both reactants are soluble) and water can be added subsequently for hydrolysis and amide bond formation.

In certain embodiments the ligation is implemented using solid phase techniques. Specifically, a first peptide attached to a resin is reacted with a phosphinothiol reagent of this invention to release the first peptide and form a phosphinothioester at the C-terminus of the first peptide. A second peptide attached to a resin at its C-terminus is derivatized with an azide group at its N-terminal amino acid. The first peptide after release from the resin is reacted with the resin-bound second peptide accompanied by hydrolysis and loss of nitrogen to generate an amide bond ligating the two peptides. The ligated peptide remains attached to the resin. The first peptide can be formed by conventional solid state methods. The second peptide can also be formed by conventional solid-phase synthetic methods in which an azido acid is the last monomer added to the peptide chain or the azido group is generated in situ from the amino group of the last amino acid. The ligated peptide (or protein) can be deprotected and, if desired, cleaved from the resin by conventional methods. Alternatively, additional cycles of N-terminal deprotection, N-terminal azido acid formation and reaction with a phosphinothioester peptide can be performed to generate longer peptides and proteins.

The ligation method of this invention can be combined with known variants of solid phase peptide synthesis. For example, the ligation methods of this invention can be employed in the synthesis of multiple antigenic peptides (MAPs) which employ a lysine-based branching core. See: Tam, J.P., *Proc. Natl. Acad. Sci. U.S.A.* 1988 85, 5409–5413.

In another specific embodiment, one of $R^P$ or $R^B$ (of Scheme 3) is a peptide or protein group and the other is a carbohydrate group. For example, $R^B$ can be a mono-, di-, tri- or polysaccharide. In another specific embodiment, one of $R^P$ or $R^B$ is a peptide or protein group and the other is a nucleoside or nucleic acid. In another embodiment, one of $R^P$ or $R^B$ is a peptide or protein group and the other is a lipid. In yet another specific embodiment, one of $R^P$ or $R^B$ is a peptide or protein group and the other is a reporter group, tag or label (e.g., a group whose presence can be detected by optical spectroscopy or mass spectrometry or other instrumental method), including a fluorescent or phosphorescent group, an isotopic label or a radiolabel.

The method of this invention is generally useful for intercepting: i.e., reacting with, any thioester intermediate in a biosynthetic pathway. In this regard, the method can be used simply to identify, tag and/or label such intermediates for identification or used to synthesize unique products through amide bond formation. The method can, for example, be used to intercept thioester intermediates in polyketide biosynthesis. The resulting coupling product can be tested for biological activity or used in the further synthesis of biologically active products, e.g., polyketides altered in structure and possibly altered in function from naturally-occurring polyketides.

The method of this invention in any of its embodiments can be implemented using solid phase methods. Either the phosphinothioester reactant or the azide reactant can be attached to a solid support material with the reactive end free. A reactant bound to a solid support having a reactive phosphinothioester group can be ligated to a free azide (i.e., where the azide reactant is not ligated to a solid support). A reactant bound to a solid support having a reactive azide group can be ligated to a free phosphinothioester. The method can be generally used to form an amide bond between two biological molecules, i.e., between two peptides, between a peptide and a carbohydrate (saccharide, sugar, etc.), between a peptide and a nucleoside, between a peptide and a lipid, etc. More specifically the method can be applied to a ligation where one of the biological molecules is attached to a solid support (or resin). A phosphinothioester peptide reactant attached to a solid support via its N-terminus can be generated, for example, by coupling of the C-terminus of the attached peptide to a phosphinothiol using a coupling reagent such as DCC, benzotriazole-1-yl-oxy-tris-pyrrolidino-phosphonium hexafluorophosphate (PyBOP). A resin-bound peptide with an azide group at its N-terminus can be generated by reaction of trifyl azide or similar reagent.

The ligation method of this invention can be employed in the creation of combinatorial libraries of peptides, proteins or various chemical species containing an amide bond. The ligation method of this invention can also be used in combination with methods of native chemical ligation for the formation of peptide and protein products of interest.

Most generally, the invention provides for the reaction of a phosphinothioester and an azide. In specific embodiments, the phosphinothioester can be prepared employing a phosphinothiol reagent. Novel phosphinothiol useful as reagents in the reactions of this invention are provided.

The invention also provides reagent kits for forming an amide bond between a phosphinothioester and an azide which comprises one or more of the phosphinothiol reagents of this invention and particularly those of the various formulas described herein. In addition the kits can contain reagents for forming an azide. The kits also optionally include resin or other solid phase materials that are appropriate for conducting the ligation of this invention using solid phase methods. The kit may also include a reagent for generating a thioester, which would later be converted to a phosphinothioester. The kit may also optionally include solvent or other reagents for carrying out the ligation, as well as instructions for conducting the reaction, and/or instructions for selection of a phosphinothiol reagent for a desired ligation.

In a specific embodiment the invention provides a kit for synthesis of peptides or proteins which comprises one or more of the phosphinothiol reagents of this invention. The kit may optionally further contain one or more amino acid side chain protecting group, one or more reagents for generating a thioester of an amino acid or peptide, or one or more reagents for generating an azido acid of an amino acid or peptide. The kit may also contain one or more amino acids, amino acid thioesters or azido acids. The kits also optionally include resin or other solid phase materials that are appropriate for conducting the ligation of this invention using solid phase method. The kit may also optionally include solvent or other reagents for carrying out the ligation, as well as instructions for carrying out the synthesis, and/or instructions for selection of a phosphinothiol reagent for a desired ligation. Reagent kits of this invention include those which comprise one or more 2-phosphinobenzenethiols or one or more phosphinomethanethiols.

DETAILED DESCRIPTION OF THE INVENTION

Figure 1:
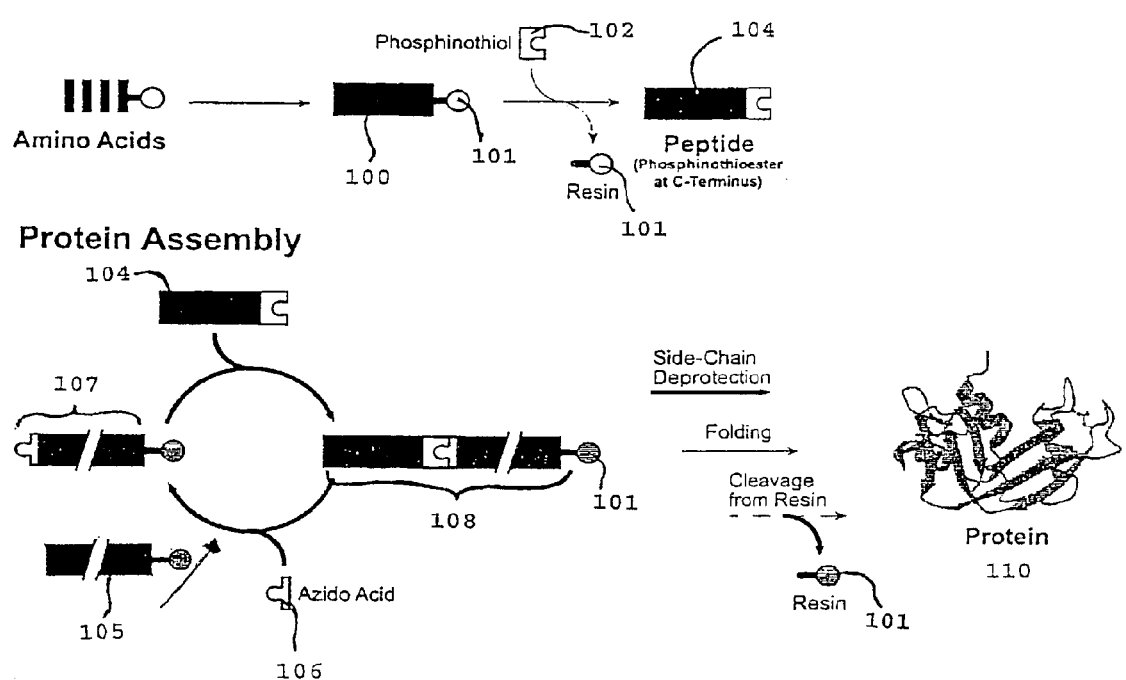
FIG. 1 is an illustration of the application of the ligation method of this invention to protein synthesis.

In the method of this invention, an amide bond is formed between a phosphinothioester and an azide. The reaction is traceless in that no atoms of the reagent are left in the ligated product. The reaction is useful in a number of applications for derivatization of amino acids, peptides, or proteins, for ligation of various biological molecules (e.g., peptides to saccharides, peptides to lipids, peptides to peptides, peptides to nucleosides or nucleic acids etc.) and particularly for the synthesis of peptide, and proteins.

Although not wishing to be bound by any particular mechanism, a likely mechanism for this reaction is illustrated in Scheme 6. The ligation begins by coupling of a phosphinothioester with an azide leading to the formation of a reactive iminophosphorane and nitrogen gas. Attack of the iminophosphorane nitrogen on the thioester leads to an amidophosphonium salt. Hydrolysis of the amidophosphonium salt produces an amide and a phosphine oxide. Significantly, no atoms from the phosphinothiol remain in the amide product.; i.e., the ligation is traceless. Scheme 6 illustrates the formation of the phosphinothioester by transesterification from a thioester, however, other methods are available for making useful phosphinothioesters. Most generally, the phosphinothioester can be formed by reaction of a phosphinothiol reagent with an activated carboxylic acid derivative. An "activated" carboxylic acid derivative is activated for nulceophilic attack, as is understood in the art, and is exemplified by thioesters, acyl halides, acyl imidazoles, activated esters, and N-acylsulfonamides (used in certain safety-catch linkers).

The ligation reactions of this invention are exemplified by the specific reactions of Schemes 7 and 8 which employ an o-phosphinobenzenethiol ($R_1R_2PC_6H_4$-o-SH), specifically o-(diphenylphosphino)benzenethiol (2) and a phosphinomethanethiol ($R_1R_2P$—$CH_2$—SH), specifically (diphenylphosphino)methanethiol 20, respectively, as phosphinothiol reagents.

The o-phosphinobenzenethiol was first selected as a reagent, because it allows a six-membered ring to form in the transition state for acyl transfer (See: Scheme 6). Moreover, $R_1R_2PC_6H_4$-o-SH does not allow for the formation of an episulfide and a stable amidophosphine $(R_1R_2PNR'C(O)R'')$ by C—P bond cleavage in the amidophosphonium salt, as would a thiol such as $R_1R_2PCH_2CH_2SH$. Further, thiophenol itself is known to effect the transthioesterification of thioesters during native chemical ligation (Dawson, P. E.; Churchill, M.; Ghadiri, M. R.; Kent, S. G. H. *J. Am. Chem. Soc.* 1997, 119, 4325–4329). The R groups on the phosphorous ($R_1$ and $R_2$) were selected to be electron-withdrawing phenyl groups which make the phosphorus less nucleophilic and thereby minimize the susceptibility of the phosphine to deleterious oxidation by $O_2(g)$.

Scheme 6

Scheme 7

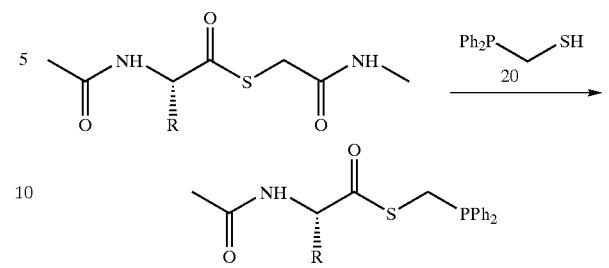

In the transformation illustrated in Scheme 7, the peptide AcPheGlyNHBn (5, where R is benzyl(Bn)) was synthesized from a phenylalanyl thioester(1, where R is Bn) and a glycyl azide (4) by the action of o-(diphenylphosphino) benzenethiol (2). o-(Diphenylphosphino)benzenethiol (2) was prepared by reaction of chlorodiphenylphosphine and ortholithiated thiophenol, as described by Block, E.; Ofori-Okai, G.; Zubieta, J. *J. Am. Chem. Soc.* 1989, 111, 2327–2329.) Thioester 3 (where R is Bn) was prepared in quantitative yield by the transthioesterification of thioester (1, where R is Bn) with an excess of phosphinobenzenethiol 2 in DMF containing diisopropylethylamine (DIEA). Phosphines are remarkable catalysts of acyl transfer reactions. Vedejs, E.; Diver, S. T. *J. Am. Chem. Soc.* 1993, 115, 3358–3359. Hence, thioester 3 (where R is Bn) likely results from the formation of an acylphosphonium salt $(Ph_2P^+(C_6H_4$-o-SH$)C(O)R)$, followed by intramolecular P- to S-acyl migration.

Excess thiol was removed by covalent immobilization to a Merrifield resin (chloromethylpolystyrene-divinylbenzene). Azide 4 (1 equivalent) was added to a solution of thioester 3 (where R is Bn) in unbuffered THF:H$_2$O (3:1), and the resulting solution was stirred at room temperature for 12 h. The reaction was then acidified by the addition of 2 N HCl, and solvents were removed under reduced pressure. Chromatography on silica gel gives purified amide 5 (where R is Bn) in 35% yield. The other major product was GlyNHBn, which can derive from the Staudinger reaction (Staudinger et al., 1919). Results of reactions of Scheme 7 where R is H are given in Table 1.

Alternative solvent conditions were also explored to determine their effect on the coupling efficiency of thioester 3 and azide 4. The reaction was performed in THF:H2O (3:1) buffered at pH 2, 4, 8, and 13.5. The reaction was also performed in methylene chloride or dimethyl formamide, followed by acidic aqueous workup. Product yields under these conditions were similar to those in unbuffered THF:H$_2$O (3:1). The ligation was also effective for coupling azide 4 with the o-phosphinobenzenethioester of N-acetyl glycine R=H in Scheme 7).

Amide 5 could have been formed by a mechanism other than that illustrated in Scheme 6. Specifically, the amide product of the ligation could have, in theory, arisen from the reduction of the azide followed by acyl transfer to the resulting amine. This mechanism was ruled out (at least as a major pathway) by a control experiment in which thioester 3 and authentic GlyNHBn was mixed under conditions (reactant concentration, solvent, temperature and time) identical to those used to effect the ligation of thioester 3 and glycl azide 4. No evidence of the formation of amide 5 was observed.

Phosphinothiol 2 has attributes sufficient to effect the ligation of this invention. Yields of the reaction using this phosphinothiol reagent were low which may be the result of the low water solubility of phosphinothiol 2. Yields may be improved by optimization of solvent for the reaction or by use of reagents that have higher solubility in aqueous solution. The ligation with phosphinothiol 2 occurs through a transition state with a six-membered ring (Scheme 6). Reducing the size of this ring in the transition state would bring the nucleophilic imide nitrogen more proximal to the electrophilic thioester carbon and result in improved yields for the ligation products.

The effect of a smaller ring transition state was assessed in the ligation reactions of Scheme 8 using the phosphinothiol 20 which should form a five-member ring transition state. Thioesters of 20 derived from AcOH, AcGlyOH, and AcPheOH were prepared by either transthioesterification or coupling with dicyclohexylcarbodiimide (DCC). After these reactions were complete by TLC analysis, Merrifield resin was used to immobilize unreacted phosphinothiol. After workup and chromatography, the purified thioesters were isolated in >90% yields.

To effect the ligation, each thioester was stirred with N$_3$CH$_2$C(O)NHBn (1 equiv) in THF/H$_2$O (3:1) at room temperature for 12 h. Solvents were removed under reduced pressure, and the product amides were purified by chromatography. The yields of amide product obtained using phosphinothiol 20 are far greater than those obtained using phosphinothiol 2 (See: Table 1). AcGlyNHBn was obtained in 91% isolated yield with 20, compared to a trace yield with 2. AcGlyGlyNHBn was obtained in 80% yield using 20, compared to 15% using 2. AcPheGlyNHBn was obtained in 92% yield with 20, compared to 35% with 2. Table 1 summarizes yields for ligation using phosphinothiols 2 and 20.

Another benefit of the use of phosphinothiol 20 is that the reagent can be regenerated from its phosphine oxide by reduction with an excess of trichlorosilane in chloroform.

TABLE 1

Yields for Ligations with Phosphinothiols 2 and 20

| phosphinothioester | azide | peptide | Yield (%) |
|---|---|---|---|
| AcS-C$_6$H$_4$-PPh$_2$ (ortho) | N$_3$CH$_2$C(O)NHCH$_2$Ph | AcGlyNHBn | <10 |
| AcS-CH$_2$CH$_2$-PPh$_2$ | N$_3$CH$_2$C(O)NHCH$_2$Ph | AcGlyNHBn | 91 |
| AcGlyS-C$_6$H$_4$-PPh$_2$ (ortho) | N$_3$CH$_2$C(O)NHCH$_2$Ph | AcGlyGlyNHBn | 15 |
| AcGlyS-CH$_2$CH$_2$-PPh$_2$ | N$_3$CH$_2$C(O)NHCH$_2$Ph | AcGlyGlyNHBn | 80 |
| AcPheS-C$_6$H$_4$-PPh$_2$ (ortho) | N$_3$CH$_2$C(O)NHCH$_2$Ph | AcPheGlyNHBn | 35 |
| AcPheS-CH$_2$CH$_2$-PPh$_2$ | N$_3$CH$_2$C(O)NHCH$_2$Ph | AcPheGlyNHBn | 92 |

$^a$ Conditions: THF/H$_2$O (3:1); room temperature; 12 h

The dramatic improvements in yield observed indicate that phosphinothiol 20 is a superior reagent for effecting the ligation of a thioester and azide to form an amide. In contrast, Bertozzi and coworkers (Saxon, E.; Armstrong, J. I.; Bertozzi, C. R. Org. Lett. 2000, 2, 2141–2143) have assessed the ability of the oxo-analogs of phosphinothiols 2 and 20 to effect a Staudinger ligation. Surprisingly, they found that Ph$_2$PC$_6$H$_4$-o-OH gives a higher yield than does Ph$_2$PCH$_2$OH. The basis for the apparent antipodal reactivity of thioesters and esters is unclear.

The high yields obtained with phosphinothiol 20 may result from the proximity of the nucleophile and electrophile in the reagent. The key intermediate in the ligation is believed to be the iminophosphorane (Scheme 6). The transition state leading from the iminophosphorane of 20 to the amidophosphonium salt contains a 5-membered ring. Both the C—S and P—N bonds in this ring have significant double-bond character. Thus, the iminophosphorane can adopt relatively few conformations. In contrast, reaction of N$_3$(CH$_2$)$_{10}$C(O)SPy and PBu$_3$ to form a lactam proceeds via a transition state with a 12-membered ring (Bosch, I; Romea, P; Urpi, F; Vilarassa, J. Tetrahedron Lett. 1993 34:4671–4674). The yield of this reaction is only 28%.

Another factor that could contribute to the high yields obtained with phosphinothiol 20 is a stable conformation that facilitates amide formation. Molecular mechanics calculations indicate that the iminophosphorane intermediate can adopt a β-turn-like conformation. A β-turn is stabilized by an O—HN hydrogen bond that defines a 10-membered ring. The thioester, imide, and amide groups of the iminophosphorane are situated in positions that correspond to the three amide groups of a β-turn. In this conformation, the nucleophilic imide nitrogen is within 3.0 Å of the electrophilic thioester carbon. Moreover, the O—HN hydrogen bond would polarize the thioester, making its carbon even more electrophilic. Finally, the bulk of the two phenyl groups could accelerate acyl transfer by increasing the fraction of iminophosphorane in the β-turn-like conformation (For examples of the "reactive rotamer effect", see: (a) Bruice, T. C.; Pandit, U. K. *J. Am. Chem. Soc.* 1960, 82, 5858–5865. (b) Jung, M. E.; Gervay, J. *J. Am. Chem. Soc.* 1991, 113, 224–232). This favorable conformation would be inaccessible during a ligation with 2, as well as in the ligation of a thioester with a non-peptidyl azide.

Phosphinothiol 20 has an additional intrinsic advantage over phosphinothiol 2. In general, aliphatic thiols (such as 20) have higher pKa values than do aromatic thiols (such as 2). Because thioester hydrolysis rates correlate inversely with their thiol pKa values (Janssen, M. J. *The Chemistry of Carboxylic Acids and Esters*; Patai, S., Ed.; Interscience Publishers: New York, 1969; pp 730–736), aliphatic thioesters have a longer half-life in aqueous solution. This long half-life is important, as the hydrolysis of the thioester, either before or after iminophosphorane formation, is likely to be a competing side reaction for the ligation.

Thus, the choice of phosphinothiol reagent is an important aspect in effecting the ligation of a thioester and azide of this invention. A phosphinothiol useful in this invention has the general structure:

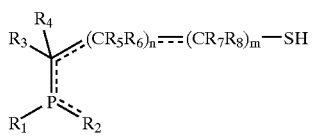

where:
n and m are 0 or integers equal to 1–3 inclusive and n+m=0–4; the dashed line indicates that a double bond may be present or that the bond may be part of an aromatic group ($R_4$, $R_6$ and $R_8$ are not present if there is a double bond between the carbons or the bond is a part of an aromatic ring, as indicated);

$R_1$ and $R_2$ are groups independently selected from aliphatic, alicyclic, heteroalicyclic, aromatic, or heteroaromatic groups which are optionally substituted, for example, with halides particularly F or Cl), OH, OR, COH, COR, COOH, COOR, or $N(R')_2$ groups where R, independent of other R, is an aliphatic, alicyclic, heteroalicyclic, aromatic or heteroaromatic group and each R', independent of other R' are hydrogen, aliphatic, alicyclic, heteroalicyclic, aromatic or heteroaromatic groups, R and R' can, in turn, be optionally substituted as listed above for $R_1$ and $R_2$; in $R_1$ and $R_2$, one or more non-neighboring $CH_2$ groups can be replaced with O, S, CO, COO, or CONR', and $R_1$ and $R_2$ together can form a ring which includes the P atom and $R_3$–$R_8$, independently, are selected from hydrogens, aliphatic, alicyclic, heteroalicyclic, aromatic or heteroaromatic groups which can be optionally substituted as listed above for $R_1$ and $R_2$, in $R_3$–$R_8$ one or more non-neighboring $CH_2$ groups can be replaced with O, S, CO, COO, or CONR' groups where each R', independent of other R' are hydrogen, aliphatic, alicyclic or aromatic groups which are optionally substituted as listed above for $R_1$ and $R_2$, and two or more of $R_3$–$R_8$ can be covalently linked to form a cyclic group, including a bicyclic group.

$R_1$ and $R_2$ groups include among others alkyl groups, alkenyl groups, cyclic alkyl, cyclic alkenyl, bicyclic groups, aromatic groups, heteroaromatic groups, ether groups, ester groups, amide groups, thioether groups, and ketone groups.

It is preferred that $R_5$–$R_8$ are not all hydrogens. It is also preferred that n+m is 0, 1 or 2. In specific embodiments, $R_3$ and $R_4$ are both hydrogens and n and m are both zero.

In specific embodiments, the phosphinothiol has the formula:

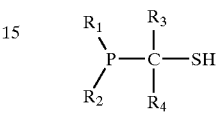

where $R_1$ and $R_2$ are aromatic or heteroaromatic groups that are optionally substituted as described above and $R_3$ and $R_4$ are as defined above. $R_3$ and $R_4$ are preferably hydrogens. $R_1$ and $R_2$ are preferably electron-withdrawing groups, including phenyl groups and substituted phenyl groups. One of $R_3$ and or $R_4$ and $R_2$ may be covalently linked to form a heteroaromatic ring which may be substituted with groups as listed above.

In other embodiments, the phosphinothiol can have the formula:

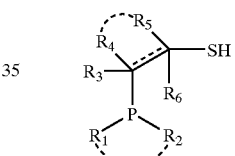

where $R_1$–$R_6$ are as defined above, $R_1$ and $R_2$ and/or $R_4$ and $R_5$ are optionally covalently linked to form a alicyclic or aromatic ring where the dashed line between carbons indicates an optional double bond or portion of an aromatic ring, $R_3$ and $R_6$ are not present if there is a double bond between carbons as indicated.

In another embodiment the phosphinothiol has the structure:

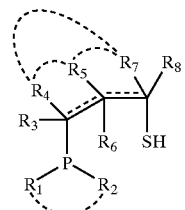

where $R_1$–$R_8$ are as defined above and $R_1$–$R_2$, or $R_4$–$R_5$, or $R_5$–$R_7$, $R_4$–$R_7$ or $R_4$–$R_5$–$R_7$ are optionally covalently linked to form an alicyclic or aromatic ring.

In further embodiments the phosphinothiol has the structure:

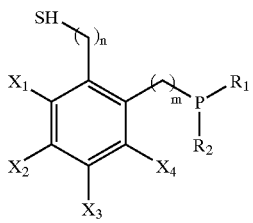

where n and m are 0 or 1, $R_1$ and $R_2$ are as defined above and $X_1$–$X_4$ are substituents on the aromatic group, two of which may be covalently linked to form an alicyclic or aromatic ring, $X_1$–$X_4$ can be aliphatic, alicyclic or aromatic groups or can be halide, OH, OR, COR, COOH, COOR (where R is aliphatic, alicyclic or aromatic), or $N(R')_2$ groups where each R', independent of other R' are hydrogen, aliphatic, alicyclic or aromatic groups R and R' are optionally substituted as listed above for $R_1$ and $R_2$.

In another embodiment the phosphinothiol has the structure:

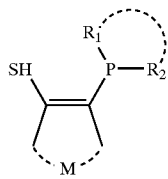

where $R_1$ and $R_2$ are as defined above and M represents an alicylic, including bicyclic, or aromatic, including heteroaromatic, ring; M can represent a phenyl ring, naphthalene (or other fused ring), a pyridine (or other heteroaromatic ring), or a cyclohexene (or other alicyclic ring) and $R_1$ and $R_2$ are optionally covalently linked to form a ring containing phosphorous.

Specific examples of this structure include:

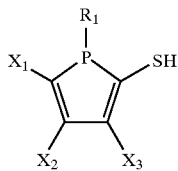 and 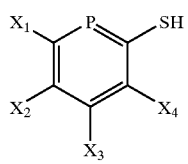

where $X_1$–$X_4$, when present, are substituents on the heteroaromatic ring and can, independently, be selected from a hydrogen, a halide, an alkyl group, an aromatic group, an OR, COR or COOR group where R is a hydrogen, an aliphatic group, an alicyclic group, an aromatic group, a CONR' or $N(R')_2$ group where each R', independent of other R', can be hydrogen, or an aliphatic or aromatic group.

In additional specific embodiments, phosphinothiol reagents of this invention include:

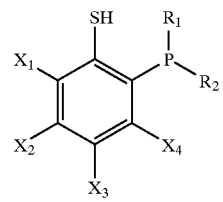

where $R_1$, $R_2$, $X_1$–$X_4$ are as defined above; and

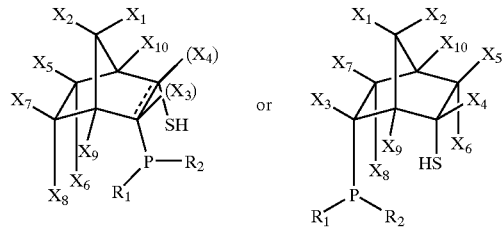

where $R_1$ and $R_2$ are as defined above, the dashed line indicates an optional double bond and $X_1$–$X_{10}$, when present, can be hydrogen, aliphatic, alicyclic or aromatic groups or can be halide, OH, OR, COR, COOH, COOR (where R is aliphatic, alicyclic or aromatic), CONR', or $N(R')_2$ groups where each R', independent of other R' are hydrogen, aliphatic, alicyclic or aromatic groups R and R' are optionally substituted as listed above for $R_1$ and $R_2$, substituents in parentheses are not present when the double bond is present.

$R_1$ and $R_2$ groups in the phosphinothiol reagent are generally selected to avoid raising the free energy of the reaction transition state by avoiding unfavorable steric or electronic interactions and to provide solubility in both organic solvents (for their synthesis) and aqueous buffers (for applications). Polyethylene glycol groups can be used, for example, to impart solubility in both organic solvents and aqueous solutions. Exemplary $R_1$ and $R_2$ groups include the polyether groups:

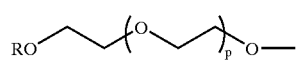

where p is 0 or an integer ranging from 1 to about 10, inclusive, preferably p is 1–4, inclusive, and R is hydrogen or an alkyl group. Carbons in the polyether groups are optionally substituted with halides, or small alkyl groups. In specific embodiments, phosphinothiol reagents of this invention in which $R_1$ and $R_2$ are phenyl groups, these phenyl groups can be substituted with one or more polyether groups to enhance the solubility of the reagent in water.

In other specific embodiments, reagents of this invention have the formulas:

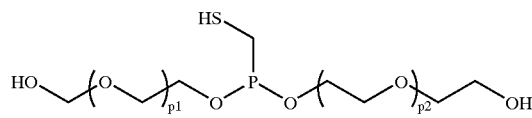

-continued

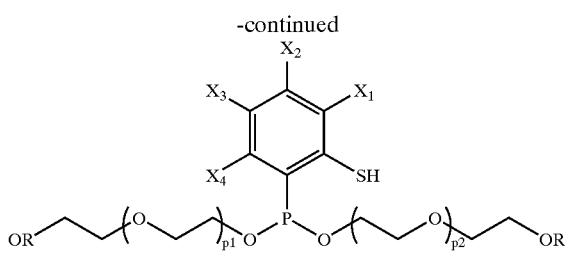

where p1 and p2 are zero or integers ranging from 1 to about 10, inclusive, R is hydrogen or an alkyl group. The integers p1 and p2 are preferably the same and preferably range from 1–4, inclusive.

These phosphinate reagents are of particular interest as a water-soluble thiol reagent for use in ligations of this invention. This type of reagent can be synthesized via the phosphoramidite $PCl_2(N(C_2H_5)_2)$, which has been used previously to phosphorylate alcohols (Perch, J. W.; and Johns, R B 1988 *Synthesis-Stuttgart* 2, 142–144). After the phosphoramidite is reacted with monoprotected tetra (ethyleneglycol), which is commercially available, the $N(C_2H_5)_2$ substituent is replaced with Cl. Ortholithiation with thiophenol and deprotection affords the desired phosphinate:

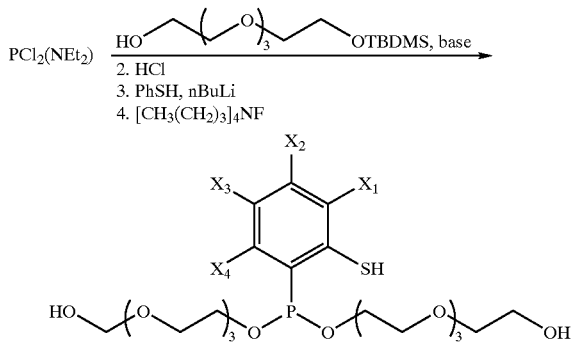

In general, $R_1$ and $R_2$ groups containing polyether groups can be synthesized by method that are well known in the art from readily available starting materials.

The reactivity of the phosphinothiol reagent can be adjusted by choice of substituents $R_1$ and $R_2$, as is known in the art. In general, these groups are selected to obtain desired reactivity with a selected azide based, at least in part, on the electronic and steric properties of the azide and to minimize sensitivity of the reagent to oxygen. Reagents that are more sensitive to oxygen are, in general, more difficult to handle and require more care in use to avoid undesired levels of oxygen that can destroy or diminish the effectiveness of the reagent. However, ligations with less reactive azide, such as azides of glycosides, can be significantly improved by use of more reactive phosphinothiol reagents. For example, the use of n-alkyl groups, such as n-butyl groups, for $R_1$ and $R_2$ groups can significantly increase reactivity of the reagent.

As an additional example, substitution of electron-donating groups (such as alkoxy groups in appropriate ring positions as is known in the art) or electron-withdrawing groups (such as $NO_2$ groups in appropriate ring positions as is known in the art, particularly p-$NO_2$) on phenyl group substituents of the phosphinothiol reagents can be used to tune the reactivity of the reagents. Addition of electron-withdrawing groups will tend to decrease the reactivity and addition of electron-donating groups on phenyl substituents which tend to increase reagent reactivity.

Phosphinothiol reagents useful in this invention can be prepared by methods well known in the art from readily available starting materials in view of the teachings herein. Reagents of this invention can be provided in kit form optionally including solvents for a desired reaction, optionally including instructions for carrying out the reaction as well as optionally including one or more azide or thioester reactants. A kit can include reagents for generating thioester and/or azides. A reagent kit may also contain one or more reagent phosphinothiols that carry a labeling group a tag or a reporter molecule for coupling to an amino acid, peptide or protein. Reagent kits can include, for example, vials or other containers containing measured relative amounts of components for carrying out a selected reaction. The reagents can be packaged and sized for use in a single ligation reaction or packaged and sized for a stepwise synthesis ligating two or more amino acids, peptides or proteins fragments.

The synthesis of the previously unknown phosplinothiols 20 is described below in Example 2 and illustrated in Scheme 9. Phenyl magnesium bromide was added to chloromethyl-phosphonic dichloride 23, and the resulting Grignard reaction refluxed for 12 h to give phosphine oxide 24. A mixture of 24 with thioacetic acid and triethylamine in dry THF was heated at reflux for 12 h. (Lamoureux, G. V.; Whitesides, G. M. *J. Org. Chem.* 1993, 58,633–641; Woycechowsky, K. J.; Wittrup, K. D.; Raines, R. T. *Chem. Biol.* 1999, 6, 871–879). After purification by flash chromatography and treatment with decolorizing charcoal, thiophosphine oxide 25 was isolated in a 54% combined yield for the two steps. An excess of trichlorosilane in chloroform for 72 h was used to reduce 25 to phosphinothioester 26 which was isolated by flash chromatography in nearly quantitative yield. Hydrolysis of the phosphinothioester 26 (Charrier, C.; Mathey, F. *Tetrahedron Lett.* 1978, 27, 2407–2410) with sodium hydroxide in methanol for 2 h gave phosphinothiol 20. (Hydrolysis under acidic conditions was unsuccessful.) During this reaction, Ar(g) was bubbled through the reaction mixture to prevent oxidation of the resultant thiol. Phosphinothiol 20 was purified by chromatography over alumina and isolated in 74% yield. The overall yield for the process in Scheme 9 was 39%.

Scheme 9

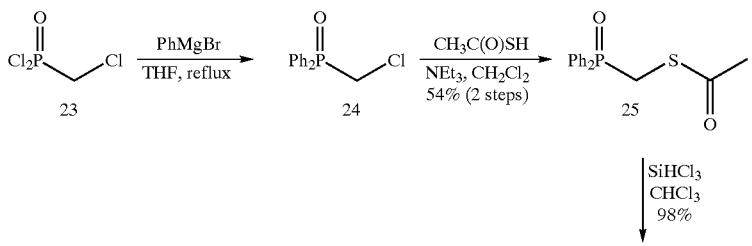

-continued

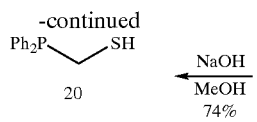 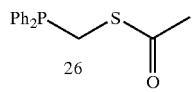

The following terms have the indicated meaning in the specification and claims:

The term aliphatic refers to hydrocarbons which are saturated or unsaturated (alkanes, alkenes, alkynes) and which may be straight-chain or branched. Aliphatic groups can be optionally substituted with various substituents or functional groups, including among others halides, hydroxy groups, thiol groups, ester groups, ketone groups, carboxylic acid groups, amines, and amides. A heteroaliphatic group is an aliphatic group that contains one or more non-carbon atoms in the hydrocarbon chain (e.g., one or more non-neighboring $CH_2$ groups are replaced with O, S or NH).

The term alicyclic refers to hydrocarbons that have one or more saturated or unsaturated rings (e.g., three to ten-membered rings) and which may be bicyclic. Alicyclic groups can include portions that are branched and/or straight-chain aliphatic in combination with cyclic hydrocarbon. Alicyclic groups can be substituted, as noted above for aliphatic groups. A heteroalicyclic group is an alicyclic group that contains one or more heteroatoms (non-carbon atoms) in the hydrocarbon chain, in a ring or in a straight-chain or branched aliphatic portion of the alicyclic group (e.g., one or more non-neighboring $CH_2$ groups can be replaced with O, S or NH).

The term aromatic refers to hydrocarbons that comprise one or more aromatic rings which may be fused rings (e.g., as in a naphthalene group). Aromatic groups can include portions that are branched and/or straight-chain aliphatic and/or alicyclic in combination with aromatic.

Aromatic groups can be substituted, as noted above for aliphatic groups. A heteroaromatic group is an aromatic group that contains one or more heteroatoms (non-carbon atoms) in an aromatic ring (e.g., a pyridine ring). A CH in an aromatic ring can be replaced with O, S or N. In any alicyclic or aliphatic portion of an aromatic groups, one or more non-neighboring $CH_2$ groups can be replaced with a heteroatom (e.g., O, S, NH).

Aliphatic, alicyclic, aromatic groups and the corresponding heteroatom-containing groups can also be substituted with functional groups as noted above. Aromatic rings can, for example, be substituted with electron-donating or electron withdrawing groups as may be desired. Electron-donating and electron-withdrawing groups being well-known in the art.

Common Amino Acids are those 20 amino acids commonly found in naturally-occurring peptides and proteins and include: glycine, alanine, valine, leucine, isoleucine, methionine, proline, phenylalanine, tryptophan, serine, threonine, asparagine, glutamine, tyrosine, cysteine, lysine, arginine, histidine, aspartic acid, and glutamic acid. $R^A$ groups include, among others, side chains or side groups of common amino acids.

Uncommon amino acids found in proteins include those with hydroxylated, alkylated, phosphorylated, formylated, and acylated side groups and, in particular, include, among others, 4-hydroxyproline, 3-methyl histidine, 5-hydroxylysine, O-phosphoserine, carboxyglutamate, acetyllysine, and N-methylarginine. Amino acid derivatives having biological activity include, among others, α-aminobutyric acid, thyroxine, citrulline, ornithine, homocysteine, S-adenosylmethionine, β-cyanoalanine, and azaserine. $R^A$ groups can also include side groups or side chains of common and uncommon amino acids and side groups of biologically-active derivatives of amino acids which are substituted with one or more halides, hydroxyls, alkyl groups, thiols, protected thiols, amino groups, protected amino groups, acetyl, ester or carboxylic acid groups.

The method of this invention can also be employed to ligate two or more amino acids that carry electrophilic side groups, such as alkyl halide side groups or epoxide side groups together or incorporate one or more of these amino acids into a peptide or proteins. Incorporation of such amino acids is difficult with conventional peptide synthesis because of the need to remove Fmoc protecting group with a base (typically piperidine). The base can also act as a nucleophile, attacking the electrophilic side chain. For example, an amino acid with an electrophilic side chain could be made by adding an azido acid containing an electrophilic side chain as the final monomer to a synthetic peptide. Deprotection of that peptide and cleavage from the resin would yield an azido peptide carrying an electrophilic side chain which could then be ligated using the method of this invention to another peptide or protein carrying a phosphinothioester group.

Amino acids that can be ligated by the method of this invention include those which are enriched in a particular isotope, e.g. $^{13}C$ or $^{15}N$-encircled amino acids. Isotopically enriched amino acids that can be employed include common or uncommon amino acids, β-amino acids and amino acids with electrophilic side groups.

Amino acids commonly found in proteins and peptides are L-amino acids. The invention will however function with D-amino acids as well as peptides and proteins containing D-amino acids. Reactants comprising $R^A$ groups may be chiral nonracemic, racemic or achiral. For synthesis of desired peptides and/or proteins reactant of appropriate chirality can be readily selected and are readily available. Reactive functional groups on $R^A$ groups can be protected with appropriate protecting groups as is known in the art. Protecting groups include among others acetyl groups, benzyl groups and other protecting groups, including those that are typically employed in art-known methods or peptide synthesis. One of ordinary skill in the art can select an art-known protecting group for use with a given functional group and a given set of reaction conditions.

The ligation as exemplified herein can be used to produce a peptide or a protein. Peptides can be synthesized as illustrated in Scheme 5 by repeated cycles of ligation to form amide bonds between amino acids. In a specific embodiment peptide synthesis can be implemented using solid phase methods in which one of the amino acids is covalently attached to a solid support or resin. A variety of resins are available in the art for use in combination with the ligation method of this invention. For example, Tentagel, PEGA, or other resins that are compatible for use in both organic and aqueous solvents are useful in combination with the ligation methods of this invention.

The ligation method of this invention can be combined with conventional methods for sequentially adding amino acids to a growing peptide chain on a solid support or resin. For example, conventional Fmoc-chemistry can be combined with one or more ligation steps which employ the phosphinothioester and azide reactants of this invention. In a specific example, one or more β-amino acids or one or more amino acids having electrophilic side groups can be introduced into a peptide chain that is being synthesized by conventional methods (e.g., Fmoc-based chemistry) using the ligation method of this invention.

FIG. 1 illustrates an exemplary approach for protein assembly employing the ligation method of this invention in combination with solid state methods. In this approach a first peptide 100 is attached via its C-terminus to a resin 101 via a thioester linkage. The first peptide is protected at its N-terminus with an appropriate protecting group. This first peptide can be synthesized, for example, by conventional solid-state peptide synthesis methods, e.g., Fmoc-methods. The bound first peptide (100) is reacted with a phosphinothiol reagent 102, such as 2 or 20, which release the N-terminal protected peptide from the resin as a phosphinothioester 104.

A second peptide 105 attached to a resin 101' at its C-terminus and having an unprotected $NH_2$ at its N-terminus (after deprotection) is reacted with an azido acid 106 to form a resin-bound peptide 107 with an azide group at its N-terminus. The azido-N-terminated peptide 107 is then reacted with the unbound N-terminal protected phosphinothioester 104 accompanied by hydrolysis and loss of nitrogen to form an amide bond which ligates the first and second peptides 108. The ligated peptide remains linked to the resin.

Additional cycles of:
deprotecting the N-terminal of the ligated peptide 108;
reacting the deprotected peptide with an azido acid to generate a resin-bound peptide with an azido acid at its N-terminus 107; and
reacting the resin-bound azido acid peptide with phosphinothioester 104 with hydrolysis and loss of nitrogen to generate resin-bound ligated peptide 108, add peptides to a growing chain of peptides. The cycles are continued until the desired larger peptide or protein 110 is synthesized.

In the approach of FIG. 1, reactive (or potentially reactive) side chains or side groups of the amino acids of the peptides to be ligated are protected from reaction using appropriate protecting groups. After the desired larger peptide or protein is synthesized, the side-chain protecting groups are removed (deprotection) using conventional methods and reagents. The larger peptide or protein is optionally subjected to conditions which facilitate desired folding and the peptide or protein product is optionally cleaved from the resin. Note that protein folding can also be accomplished after cleavage of the protein from the resin.

Peptides formed by conventional solid-state methods typically range in length from about 30–50 amino acids, so that a protein of about 300 amino acids in length would require a about 8–10 addition cycles.

Peptide thioesters can arise from conventional solid-phase peptide synthesis (e.g., Fmoc-based solid-phase synthesis) (Ingenito, R.; Bianchi, E.; Fattori, D.; Pessi, A. *J. Am. Chem. Soc.* 1999, 121, 11369–11374; Shin, Y.; Winans, K. A.; Backes, B. J.; Kent, S. B. H.; Ellman, J. A. Bertozzi, C. R. *J. Am. Chem. Soc.* 1999, 121,11684–11689; Swinnen, D.; Hilvert, D. *Org. Lett.* 2000, 2,2439–2442) or rDNA technology (Muir et al., 1998; Evans, Jr., et al., 1998; Ayers, et al., 2000; Holford et al., 1998; Cotton et al., 1999; Evans, Jr., 2000). Alternatively, peptides can be generated from natural, e.g., as fragments of proteins, or by expression in recombinant systems. These peptides can be derivatized to thioesters using conventional reagents and methods. Peptides from whatever source can be derivatized (at their N-terminal with azide, for example, by reaction of the a-amino group of a protected peptide with $CF_3SO_2N_3$.(Zaloom, J.; Roberts, D. C. *J. Org. Chem.* 1981, 46, 5173–5176). Azide groups can also be added to peptide amino groups by conventional reagents and methods.

Solid support materials, e.g., resin, appropriate for use in organic and aqueous solvents as are employed in the ligations of this invention are known in the art and one of ordinary skill in the art can readily select support materials that are compatible with the synthetic steps to be performed. Of particular interest are the use of safety-catch linkers to resins for the synthesis of peptides which can thereafter be ligated using the methods of this invention. Native chemical ligation has been implemented using a safety-catch linker. See: Brik, A.; Keinan E.; Dawson, P. E.; *J. Org. Chem.* 2000 (June) 16:65(12):3829–3835. Scheme 10 illustrates the synthesis of a peptide by conventional methods on a safety-catch resin and release of the peptide using a phosphinothiol reagent of this invention.

One of ordinary skill in the art can readily synthesize resin-bound peptides by conventional methods that are compatible with the ligation steps of this invention. In a specific embodiment, peptide can be linked to a resin for solid phase synthesis via a photolabile linkage group. Such a group is cleaved by irradiation at an appropriate wavelength.

A variety of side-group protecting groups useful in the method of this invention are known in the art and can be readily selected for given reaction conditions. Methods for side-chain deprotection and cleavage of peptides and proteins from resins without substantial detriment to the product peptides or proteins are known in the art. Azide-substituted amino acids are readily available from commercial sources or from application of routine methods that are well known in the art.

Scheme 10

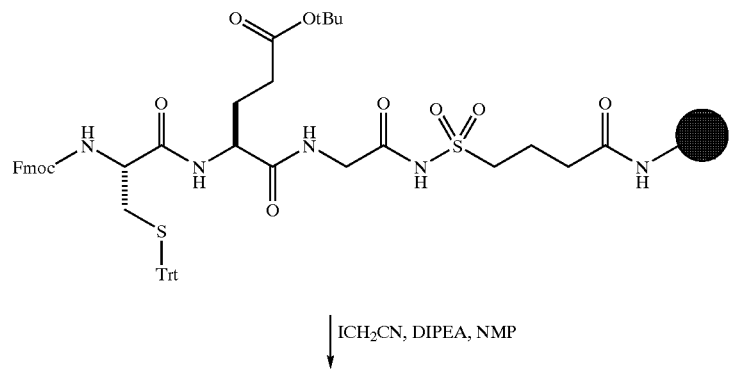

$ICH_2CN$, DIPEA, NMP

-continued

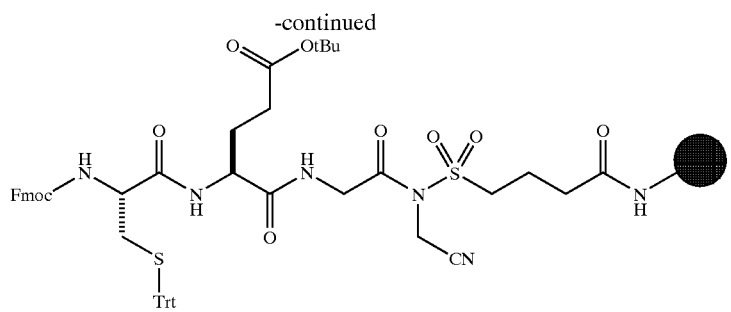

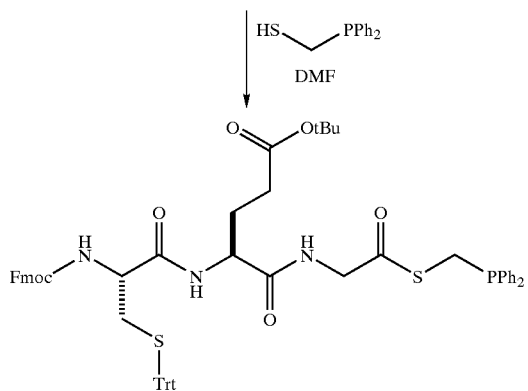

Reactants and reagents employed in the methods of this invention are readily available either from commercial sources or can be prepared using methods that are well-known in the art in view of the description herein. For example, azido glycosides (e.g., azido mannose) and azido nucleosides (e.g., AZT) can be prepared by methods know in the art. Thioesters of various biologically interesting molecules are also readily accessible by well-known methods. Phosphinothioesters are prepared by methods illustrated herein or art-known methods and can, in particular, by synthesized by transthioesterification or coupling reactions. Exemplary methods are provided in the examples. Azido acids are readily accessible (Zaloom, J.; et al., 1981) and can be used in solid-phase synthesis (Meldal, M.; Juliano, M. A.; Jansson, A. M. *Tetrahedron Lett.* 1997, 38, 2531–2534). Thioesters of various biologically interesting molecules, such as sialic acid or certain lipids, are also readily accessibly by known methods.

Ligation methods of this invention of this invention employing phosphinothiol 20 are particularly useful to enable facile protein synthesis.

Further, the ligation method of this invention is orthogonal to native chemical ligation (as well as other effective coupling strategies, Tam, J. P.; Lu, Y. A.; Chuan-Fa, L.; Shao, J. *Proc. Natl. Acad. Sci. U.S.A.* 1995, 92, 12485–12489; Tam, J. P.; Yu, Q.; Miao, Z. *Biopolymers* 2000, 51, 311–332), and hence expands the scope of protein synthesis. Moreover, both coupling reactions can be performed on unprotected peptides in the presence of $H_2O$.

Scheme 11 depicts the simplest proteins that are accessible by native chemical ligation alone, the Staudinger ligation alone, and a sequential combination of the two methods. The use of thiol- or azide-protecting groups can extend the versatility of these methods even further.

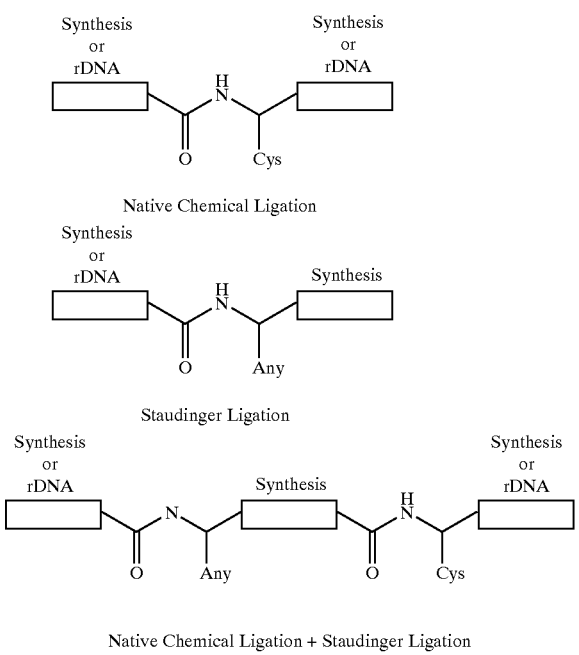

The ligation method of this invention can also be used in general to intercept natural thioester intermediates in biosynthetic pathways. A number of biosynthetic pathways proceed via the elaboration of thioester intermediates. (For recent reviews, see: Katz, L *Chem. Rev.* 1997, 97, 2557–2575; Khosla, C. *Chem. Rev.* 1997, 97, 2577–2590; Marahiel, M. A.; Stachelhaus, T.; Mootz, H. D. *Chem. Rev.* 1997, 97, 2651–2673; von Dohren, H; Keller, U.; Vater, J.;

Zocher, R *Chem. Rev.* 1997, 97, 2675–2705; Cane, D. E.; Walsch, C. T.; Khosla, C. *Science* 1998, 282, 63–68; Konz, D.; Marahiel, M. A. *Chem. Biol.* 1999, 6, R39–R48; Keating, T. A; Walsch, C.T. *Curr. Opin. Chem. Biol.* 1999,. 3, 598–606.)

For example, both the biosynthesis of polyketides and the nonribosomal biosynthesis of proteins proceed by thioester intermediates. Interception of these intermediates with a phosphinothiol allows for ligation to an azide forming an amide bond. Significantly, ligation of a biosynthetic library of thioesters with a chemical library of azides is a facile means to increase molecular diversity. Chemical libraries formed using the ligation method of this invention can be screened for biological function by a variety of methods known in the art.

As exemplified in FIG. 1, the ligation methods of this invention can be implemented in solid phase synthesis. Either the thioester or the azide reactants in the ligation can be bound to a solid surface or support material. The use of solid phase methods is particularly beneficial for the synthesis of peptides by repeated cycles of the ligation of this invention. The use of solid phase methods is also beneficial for the ligation of two or more peptides or proteins to make larger peptides, or proteins. Reaction of a bound thioester with the phosphinothiol reagent and unbound azide or a bound azide with an unbound thioester and the phosphinothiol reagent will result in a bound ligation product. Conventional methods for attaching various species to a solid surface or support material can be used to attach either thioester reactants or azide reactant to such materials.

The ligation of the phosphinothiol and azide of this invention is preferably conducted in a mixed organic/aqueous solvent, such as mixtures of THF and water. Water participates in hydrolysis of the amidophosphonium salt to produce the desired amide. THF or other organic solvent (e.g., methylene chloride, DMF) is included to solubilize the phosphinothiol reagent or the reactants. Thus, the amount of water present in the solvent must be sufficient to effect desired hydrolysis. With phosphinothiol reagents that are sufficiently water soluble the ligation can be preformed in aqueous solvent.

Those of ordinary skill in the art in view of the description herein will appreciate that the specific reaction conditions (e.g., solvent, reaction temperature and reaction time) employed for ligation may vary dependent upon the specific reagents (e.g., phosphinothiol), reactants and products (e.g., amino acids, peptides or proteins) of a given reaction. Reaction conditions can be readily optimized by methods understood in the art.

Reactions employing phosphinothiol 2 were at one time carried out by acidifying (with HCl) prior to product purification. It is believed that it is not necessary to add acid to the reaction mixture to obtain the desired amide product, at least when phosphinothiol 20 is employed. Acidification of the reaction mixture may, however, affect product yields. Hydrolysis may also be facilitated in appropriate cases by addition of base to the reaction mixture.

Products of the ligation methods of this invention are purified by conventional methods that are well-known in the art. Any of a wide variety of methods for peptide and protein purification can be employed in combination with the methods of this invention.

A process based on the ligation of thioesters and azides is a valuable source of proteins for both basic research and drug discovery. Methods of this invention can be used as a reliable route to homogeneous, correctly folded proteins with potent biological activity. The user of this invention can apply tools of synthetic and medicinal chemistry to make and improve protein reagents and protein therapeutics.

The following examples are intended to further illustrate the invention and are in no way intended to limit the invention.

EXAMPLES

General Experimental

Chemicals and solvents were purchased from Aldrich® with the exception of N-methylmercaptoacetamide (Fluka®), bromoacetyl bromide (Acros®), and Merrifield resins (Novabiochem®). Merrifield resins (chloromethylpolystyrene-divinylbenzene) used were 200–400 mesh (substitution 0.63 mmol/g) and 70–90 mesh (1.26 mmol/g). Reactions were monitored by thin layer chromatography using Whatman® TLC plates (AL SIL G/UV) and visualized by UV or $I_2$. NMR spectra were obtained using Bruker AC-300 or Varian UNITY-500 spectrometers. Phosphorus-31 NMR spectra were proton-decoupled and referenced against an external standard of deuterated phosphoric acid. Mass spectra were obtained using electrospray ionization (ESI) techniques at the University of Wisconsin Biotechnology Center.

Example 1

Thioesters 1 (Where R is H or Bn) (Referring to Scheme 7)

An N-acetyl amino acid (N-acetyl glycine or N-acetyl phenylalanine) and one equivalent of N-methylmercaptoacetamide (NMA) were charged to a flame-dried reaction vessel under an argon atmosphere and dissolved in dry DMF (N,N-dimethylformamide) to a final concentration of 0.5–0.7 M. DCC (dicyclohexylcarbodiimide, 1.1 equivalents) was added and the mixture was stirred at room temperature for 10–12 h. The DCU (dicyclohexylurea) by-product was filtered off and solvent was removed under reduced pressure. Products were recrystallized from $CH_2Cl_2$ and hexanes. Thioester 1 R=H was obtained in a 90% yield and thioester 1 ®=Bn) was obtained in a 92% yield. Thioester 1 ®=H). $^1H$ NMR (DMSO-$d_6$, 1:1, 300 MHz) δ 8.62 (t, J=6 Hz, 1 H), 8.05 (bs, 1 H), 4.00 (d, J=6 Hz, 2 H), 3.56 (s, 2 H), 2.59 (d, J=4.5 Hz, 3 H), 1.93 (s, 3 H) ppm; $^{13}C$ NMR (DMSO-$d_6$, 75 MHz) δ 197.95, 170.07, 167.13, 48.54, 31.81, 25.84, 22.26 ppm; MS (ESI) m/z 204.25 ($M^+$=204.9, fragments at 105.9, 100.0, 72.0). Thioester 1 ®=Bn). $^1H$ NMR (CDCl$_3$:CD$_3$OD, 1:1, 500 MHz) δ 7.30–7.27 (m, 2 H), 7.24–7.19 (m, 3 H), 4.79 (dd, J=10, 5 Hz, 1 H), 3.57 (apparent 1, J=15 Hz, 2 H), 3.24 (ABX, J-14, 5 Hz, 1 H), 2.91 (ABX, J=14, 10 Hz, 1 H), 2.76 (s, 3 H), 1.95 (s, 3 H) ppm; $^{13}C$ NMR (CDCl$_3$:CD$_3$OD, 1:1, 125 MHz) δ 200.26, 172.83, 169.92, 136.93, 129.47, 128.98, 127.40, 61.24, 37.73, 32.72, 26.72, 22.40 ppm; MS (ESI) m/z 294.37 ($ME^+$—295.0 fragments at 190.0, 162.2, 120.2).

2-Phosphinobenzenethiol (2)

Compound 2 (o-was prepared by the method of Block, E.; Ofori-Okai, G.; Zubieta, J. *J. Am. Chem. Soc.* 1989, 111, 2327–2329 and NMR data ($^1H$ and $^{31}P$) correlated with their published data. Additional spectral data. $^{13}C$ NMR (CDCl$_3$, 125 MHz) δ 137.71 (d, J=30 Hz), 135.93 (d, J=8.75 Hz), 135.35 (d, J=9.75 Hz), 133.98, 133.83, 130.45, 129.25, 129.00, 128.67 (d, J-6.75 Hz), 125.92 ppm; MS (ESI) m/z 294.35 ($M^+$—295.0).

Thioesters 3 (R=H or Bn)

Method A (transthioesterification). Compound 1 (1 equivalent) and compound 2 (10 equivalents) were charged to a flame-dried reaction vessel under an argon atmosphere and dissolved in dry DMF (0.25 M). Dry argon was bubbled through the mixture and diisopropylethylamine (DIEA, 5 equivalents) was added. The mixture was stirred for 12 h after which another 5 equivalents of DIEA were added. Merrifield resin (Both high and low loading capacity were used on different occasions) having a loading capacity at least equivalent to the molar amount of compound 2 was added to the mixture to remove excess phosphinobenzenethiol and N-methylmercaptoacetamide. This mixture was stirred for an additional 12 h under argon and the resin was filtered off. Solvent was removed under reduced pressure, the residue was taken up in $CH_2Cl_2$ and the insoluble DIEA salts were filtered off. Solvent was again removed and the residue was used in the subsequent coupling reaction without further purification. The reaction proceeded in quantitative yield, as judged by TLC.

Method B (DCC coupling). Compound 1 (R=H or R=Bn) (1 equivalent) and compound 2 (1 equivalent) were added to a flame-dried reaction vessel under an argon atmosphere. DCC (1.1 equivalents) was added and the reaction was stirred for 12 h. The DCU by-product was filtered off and solvent was removed under reduced pressure. Compounds 3 R=H or R=Bn) was purified by chromatography (silica gel, ethyl acetate:hexanes 1:1 followed by 100% ethyl acetate). Compound 3 (R=H) was obtained in 61% yield and compound 3 (R=Bn) was obtained in 52% yield. Thioester 3 (R=H). $^1H$ NMR ($CDCl_3$, 500 MHz), 7.48 (ddd, J-5.5, 4, 1.5 Hz, 1 H), 7.41 (td, J=7.5, 1.5 Hz, 1 H), 7.37–7.32 (m, 7 H), 7.28–7.24 (m, 4 H), 6.92 (ddd, J=7.5, 3, 1.5 Hz, 1 H), 5.86 (bs, 1H0, 4.07 (d, J=6 Hz), 2 H), 2.02 (s, 3 H) ppm; $^{13}C$ NMR ($CDCl_3$, 125 MHz) 194.83, 170.63, 144.04, 138.00, 136.68 (d, J=10.75 Hz), 134.84, 134.69, 130.95, 130.30, 129.68, 129.34 (d, J=6.88 Hz), 49.78, 23.69 ppm; $^{31}P$ NMR ($CDCl_3$, 202 Hz) −9.91 ppm; MS (ESI) m/z 393.44 ($M^+$—394.2, fragments at 295.2, 225.2). Thioester 3 (R=Bn). $^1H$ NMR ($CDCl_3$, 500 MHz). 7.44 (ddd, J=7.5, 4, 1.5 Hz, 1 H), 7.40 (td, J=7.5, 1.5 Hz, 1 H), 7.36–0.31 (m, 7 H), 7.28–7.21 (m, 7 H), 7.12–7.10 (m, 2 H), 6.89 (ddd, J=8, 3, 1 Hz, 1 H) 5.63 (d, J=13.5 Hz, 1 H), 4.92 (m, 1 H), 2.95 (ABX, J=14.5, 5.5 Hz, 1 H), 2.64 (ABX, J-14, 8 Hz, 1 H), 1.91 (s, 3 H) ppm; $^{13}C$ NMR ($CDCl_3$, 125 MHz) 197.47, 170.43, 137.94, 136.40, 134.83, 134.75, 134.67, 134.58, 130.79, 130.30, 129.94, 129.64 (d, J=5.9 Hz), 129.33, 127.77, 60.29, 38.24, 23.79 ppm; $^{31}P$ NMR ($CDCl_3$, 202 Hz) −10.33 ppm; MS (ESI) m/z 483.56 ($MH^+$—484.2, fragment at 295.2).

Azide 4

Benzyl amine (20.4 mL, 186 mmol) and methylene chloride (186 mL) were added to a flame-dried reaction vessel under an argon atmosphere and the solution was cooled to 0□C in an ice bath. Bromoacetyl bromide (8.1 mL, 93 mmol) was added dropwise to the solution. The HBr salt of benzyl amine precipitated from solution almost immediately. The reaction was warmed to room temperature and stirred for 1 h. The benzyl amine salt was filtered off and the organic phase was washed twice with 2 N HCl (75 mL). The organic layer was dried over anhydrous magnesium sulfate, filtered, and solvent was removed under reduced pressure. The resulting white solid was dissolved in THF (200 mL) and water (50 mL). Sodium azide (30.3 g, 466 mmol) was added and the mixture was stirred vigorously at reflux for 17 h. The organic layer was then separated from the aqueous layer, washed twice with saturated brine solution (75 mL), dried over anhydrous magnesium sulfate and filtered, and solvent was removed under reduced pressure. Azide 6 was isolated in 98% yield and was used without further purification. Spectral data. $^1H$ NMR ($CDCl_3$, 300 MHz) 7.39–7.27 (m, 5 H), 6.71 (bs, 1 H), 4.47 (d, J=5.7 Hz), 4.00 (s, 2 H) ppm; $^{13}C$ NMR ($CDCl_3$, 125 MHz) 166.66, 137.39, 128.43, 127.45, 127.35, 52.06, 43.08 ppm; MS (ESI) m/z 190.20 ($MH^+$=191.0, fragment at 91.2).

Amides =(R=H or Bn)

Thioesters 3 (R=H or Bn) (1 equivalent) and azide 6 (1 equivalent) were dissolved in $THF:H_2O$ (3:1) to a concentration of 0.2 M. A yellow color, presumably from liberated thiolate, formed quickly. The mixture was stirred at room temperature for 12–16 h and was then acidified with 2 N HCl until the yellow color became clear. Solvent was removed under reduced pressure and the amide products were separated from the phosphine oxide byproducts (also characterized spectrally, data not shown) by chromatography (silica gel, 2.5–10% methanol in methylene chloride). Purification frequently required multiple columns. Yields for amides 7 and 8 ranged from 15 to 40%. Amide 5 (R=H). $^1H$ NMR ($CDCl_2$:$CD_3OD$, 1:1, 500 MHz) 7.33–7.22 (M, 5 H), 4.41 (s, 2 H), 3.92 (s, 2 H), 3.86 (s, 2 H), 2.01 (s, 3 H) ppm; $^{13}C$ NMR ($CDCl_3$:$CD_3OD$, 1:1, 125 MHz) 173.56, 171.52, 170.67, 138.83, 129.04, 218.02, 127.78, 43.70, 43.62, 43.16, 22.45 ppm; MS (ESI) m/z 263.29 ($MH^+$—264.0). Amide 5 (R=Bn). $^1H$ NMR ($CDCl_3$:$CD_3OD$, 1:1, 500 MHz). 7.32–7.19 (m, 10 H), 4.48 (apparent t, J-7.5 Hz, 1 H), 4.44 (d, J=15 Hz, 1 H), 4.34 (d, J=14.5 Hz, 1 H), 3.95 (d, J=16.5 Hz, 1 H), 3.71 (d, J=16.5 Hz, 1 H), 3.11 (dd, J=13.5, 7 Hz, 1 H), 2.94 (dd, J=14, 8 Hz, 1 H), 1.88 (s, 3 H) ppm; $^{13}C$ NMR ($CDCl_3$:$CD_3OD$, 1:1, 125 MHz). 173.42, 172.81, 170.34, 138.61, 137.18, 129.55, 129.01, 128.93, 127.86, 127.68, 127.40, 56.12, 43.53, 43.18, 37.76, 22.36 ppm; MS (ESI) m/z 353.42 ($MNa^+$=376.2, $MH^+$=354.2 fragments at 165.2, 120.2, 91.2).

Example 2

Phosphine Oxide 24 (Referring to Scheme 9)

Chloromethylphosphonic dichloride 23 (20 g, 120 mmol) was dissolved in freshly distilled THF (240 mL). A solution of phenylmagnesium bromide (1.0 M) in THF (240 mL, 240 mmol) was added dropwise over 1 h. The resulting mixture was stirred at reflux for 24 h. The reaction was then quenched by the addition of water (20 mL), and solvent was removed under reduced pressure. The residue was taken up in $CH_2Cl_2$ and washed once with water (50 mL) and once with brine (50 mL). The organic layer was dried over anhydrous $MgSO_4(s)$ and filtered, and solvent was removed under reduced pressure. The residue was purified by flash chromatography (silica gel, 3% methanol in methylene chloride). Phosphine oxide 24 was isolated as a white solid in 63% yield. Spectral data. $^1H$ NMR ($CDCl_3$, 500 MHz) δ 7.84–7.79 (m, 4 H), 7.62–7.58 (m, 2 H), 7.54–7.50 (m, 4 H), 4.05 (d, J=7 Hz, 2 H) ppm; $^{13}C$ NMR ($CDCl_3$, 125 MHz) δ 132.60, 131.51 (d, J=9.6 Hz), 129.64 (d, J=103.9 Hz), 128.72 (d, J=11.6 Hz), 37.64 (d, J=71.9 Hz) ppm; $^{31}P$ NMR ($CDCl_3$, 202 Hz) 28.46 ppm; MS (ESI) m/z 250.03 ($MH^+$=251.0, $M_2H^+$—501.2 fragments at 173.0, 143.0, 91.0).

Compound 25

Phosphine oxide 24 (18.94 g, 75.6 mmol) was dissolved in THF (0.45 L). Thioacetic acid (34.3 mL, 480 mmol) was added, and the resulting solution was cooled in an ice bath. Ar(g) was bubbled through the reaction mixture for 1 h. Diisopropylethyl amine (83.6 mL, 480 mmol) was added dropwise, and the resulting mixture was heated at reflux for 24 h. Another aliquot of thioacetic acid (35.2 mL, 492 mmol) was then added, followed by triethyl amine (60.0 mL, 492 mmol). The reaction mixture was heated at reflux for another 24 h, after which solvent was removed under reduced pressure in a well-ventilated hood (stench!). The resulting black oil was dissolved in methylene chloride (0.35 L), and this solution was washed with 2 N HCl (0.15 L), saturated sodium bicarbonate solution (0.15 L), and brine (0.15 L). The organic layer was dried over anhydrous MgSO$_4$(s) and filtered. Activated charcoal was added to this solution, which was then heated at reflux for 30 min. The activated charcoal was removed by filtration, solvent was removed under reduced pressure, and the residue was purified by flash chromatography (silica gel, 70% ethyl acetate in hexanes). The pooled fractions were dissolved in methylene chloride (0.30 L), and the treatment with activate charcoal was repeated. Upon solvent removal, thioacetate 25 was isolated as an orange oil that solidified upon standing at room temperature. The yield for this reaction was 85%. Spectral data. $^1$H NMR (CDCl$_3$, 500 MHz) 7.80–7.75 (m, 4 H), 7.56–7.52 (m, 2 H), 7.49–7.46 (m, 4 H), 3.77 (d, J=8 Hz, 2 H), 2.25 (s, 3 H) ppm; $^{13}$C NMR (CDCl$_3$, 125 MHz) 192.82, 132.11, 131.05 (d, J=102 Hz), 130.86 (d, J=9.75 Hz), 128.46 (d, J=12.63 Hz), 29.83, 27.12 (d, J=69.88 Hz) ppm; $^{31}$P NMR (CDCl$_3$, 202 MHz) 29.14 ppm; MS (ESI) m/z 290.05 (MH$^+$=291.0, M$_2$H$^+$=581.2, fragments at 249.2, 171.0, 125.0).

Phosphine 26

Thioacetate 25 (18.65 g, 64.2 mmol) was dissolved in anhydrous chloroform (160 mL). To this solution was added trichlorosilane (97 mL, 963 mmol), and the mixture was stirred under Ar(g) for 72 h. Solvent was removed under reduced pressure (note: excess trichlorosilane in the removed solvent was quenched by slow addition of saturated sodium bicarbonate solution in a well-ventilated hood), and the residue was purified by flash chromatography (silica gel, 3% methanol in methylene chloride). Phosphine 26 was isolated as a white solid in 98% yield. Spectral data. $^1$H NMR (CDCl$_3$, 500 MHz) δ 7.43–7.40 (m, 4 H), 7.33–7.30 (m, 6 H), 3.50 (d, J=4 Hz, 2 H), 2.23 (s, 3 H) ppm; $^{13}$C NMR (CDCl$_3$, 125 MHz) δ 194.01, 136.42 (d, J=13.6 Hz), 132.28 (d, J=19.4 Hz), 128.69, 128.11 (d, J=6.8 Hz), 29.83, 25.41 (d, J=23.4 Hz) ppm; $^{31}$P NMR (CDCl$_3$, 202 MHz) −15.11 ppm; MS (ESI) m/z 274.06 (MH$^+$=275.0, fragments at 233.0, 199.2, 121.2).

(Diphenylphosphino)methanethiol (20)

Phosphine 26 (17.27 g, 63.0 mmol) was dissolved in anhydrous methanol (0.40 L), and Ar(g) was bubbled through the solution for 1 h. Sodium hydroxide (5.04 g, 127 mmol) was then added, and the mixture was stirred under argon for 2 h. Solvent was removed under reduced pressure, and the residue was dissolved in methylene chloride (0.30 L). The resulting solution was washed with 2 N HCl (2×0.10 L) and brine (0.10 L). The organic layer was dried over MgSO$_4$(s) and filtered, and solvent was removed under reduced pressure. The residue was purified by flash chromatography (alumina, 25% ethyl acetate in hexanes). (Diphenylphosphino)methanethiol 20 was isolated as a clear oil in 74% yield. Spectral data. $^1$H NMR (CDCl$_3$, 300 MHz). 7.41–7.38 (m, 4 H), 7.33–7.26 (m, 6 H), 3.02 (d, J=7.8 Hz, 2 H), 1.38 (t, J=7.5 Hz, 1 H) ppm; $^{13}$C NMR (CDCl$_3$, 75 MHz). 132.54 (d, J=17.1 Hz), 128.86, 128.36, 128.14, 20.60 (d, J=21.7 Hz) ppm; $^{31}$P NMR (CDCl$_3$, 121 MHz) −7.94 ppm; MS (ESI) m/z 232.05 (MH$^{30}$ —233.0, fragments at 183.0, 155.0, 139.0, 91.2).

AcPheCH$_2$PPh$_2$ (Table 1)

Method A (transthioesterification). Phosphinothiol 20 (500 mg, 2.2 mmol) was dissolved in dry TBF (5 mL). The solution was deoxygenated by bubbling Ar(g) for 0.5 h. To this solution was added NaH (51.6 mg, 2.2 mmol). The mixture formed a slurry to which was added DMF (2 mL0 to dissolve any precipitate. The N-methylmercaptoacetamide (NMA) thioester of N-acetylphenylalanine (63 mg, 0.22 mmol) was added, and the reaction mixture was stirred for 8 h. Unreacted Phosphinothiol 20 was removed by adding Merrifield resin (1.5 g, 1.26 mmol/g), stirring for 6 h, and removing the resin by filtration. The residue was purified by flash chromatography (silica gel, 50% ethyl acetate in hexanes). AcPheSCH$_2$PPh$_2$ was isolated as a white solid in 92% yield.

Method B (DCC coupling). Compound 20 (500 mg, 2.15 mmol) and N-acetylphenylalanine (446 mg, 2.15 mmol) were dissolved in DMF (15 mL) under Ar(g). 1,3-Dicyclohexylcarbodiimide (DCC; 489 mg, 2.37 mmol) was then added, and the reaction mixture was stirred for 12 h at room temperature. The 1,3-dicyclohexylurea (CU) by-product was removed by filtration, solvent was removed under reduced pressure, and the residue was purified by chromatography as in Method A. AcPheSCH$_2$PPh$_2$ was isolated as a white solid in 84% yield. Spectral data. $^1$H NMR (CDCl$_3$, 300 MHz) δ 7.44–7.39 (m, 4 H), 7.35–7.33 (m, 6 H), 7.26–7.21 (m, 3 H), 7.11–7.09 (m, 2 H), 6.29 (d, J=8.4 Hz, 1 H), 4.98–4.91 (m, 1 H), 3.57–3.44 (m, 2 H), 3.09 (dd, J=14.1, 5.4 Hz, 1 H), 2.93 (dd, J=14.1, 7.5 Hz, 1 H), 1.88 (s, 3 H) ppm; $^{13}$C NMR (CDCl$_3$, 125 MHz) δ 198.901, 169.86, 135.50, 132.62 (d, J=19.4 Hz), 129.11 (d, J-9.8 Hz) 128.79 (d, J=35.9 Hz), 128.50, 128.45, 126.99, 59.56, 37.99, 25.61 (d, J=24.4 Hz), 22.88 ppm; $^{31}$P NMR (CDCl$_3$, 121 MHz −44.55 ppm.

AcGlyCH$_2$PPh$_2$ (Table 1)

Method A. Phosphinothiol 20 (500 mg, 2.2 mmol) was dissolved in 5 mL of dry THF. The solution was deoxygenated by bubbling Ar(g) for 0.5 h. To this solution was added NaH (51.6 mg, 2.2 mmol). The mixture formed a slurry to which was added DMF (2 mL) to dissolve any precipitate. The NMA thioester of N-acetylglycine (44 mg, 0.22 mmol) was added, and the reaction mixture was stirred for 8 h. Unreacted phosphinothiol 20 was removed by adding Merrifield resin (1.5 g, 1.26 mmol/g), stirring for 6 h, and removing the resin by filtration. The residue was purified by flash chromatography (silica gel, 50% ethyl acetate in hexanes). AcGlyCh$_2$PPh$_2$ was isolated as a white solid in 91% yield.

Method B. Phosphinothiol 20 (100 mg, 0.43 mmol) and N-acetylglycine (55 mg, 0.47 mmol) were dissolved in DMF (3 mL) under Ar(g). DCC (98 mg, 0.47 mmol) was added, and the mixture was stirred for 12 h at room temperature. The DCU by-product was removed by filtration, solvent was removed under reduced pressure, and the residue was purified by chromatography as in Method A. AcGlyCH$_2$PPh$_2$ was isolated as a white solid in 67% yield. Spectral data. $^1$H NMR (CDCl$_3$, 300 MHz) δ 7.46–7.39 (m, 4 H), 7.38–7.36 (m, 6 H), 6.44 (bs, 1 H), 4.15 (d, J=5/7 Hz, 2 H), 3.53 (d, J=3.6 Hz, 2 H), 2.02 (s, 3 H) ppm; $^{13}$C NMR (CDCl$_3$, 75 MHz) δ 196.13, 170.29, 136.45 (d, J=13.6 HZ), 132.62 (d, J=19.1 Hz), 129.17, 128.54 (d, J=6.7 Hz), 48.98, 25.29 (d, J-24.2 Hz), 22.84 ppm; $^{31}$P NMR (CDCl$_3$, 121 MHz) δ −15.20 ppm; MS (ESI) m/z 331.08 (MH$^+$—332.2, MK$^+$—370.0).

AcGlyNHBn (Table 1)

Thioester AcSCH$_2$PPh$_2$ (271 mg, 0.99 mmol) and azide N$_2$GlyNHBn (187 mg, 0.99 mmol) were dissolved in THF/H$_2$O (3:1, 9.4 mL), and the mixture was stirred at room temperature for 12 h. Solvent was removed under reduced pressure, and the residue was purified by flash chromatography (silica gel, 5% methanol in methylene chloride). AcGlyNHBn was obtained as a white solid in 91% yield. Spectral data. $^1$H NMR (CDCl$_3$:CD$_3$OD, 1:1, 125 MHz) δ 171.76, 169.37, 137.49, 127.83, 126.77, 126.59, 42.50, 42.09, 21.32 ppm; MS (ESI) m/z 206.11 (MH$^+$—207.0).

Experimental and spectral information for the other amide products and for the NMA thioesters can be found in the Supporting Information of Nilsson, B. L.; Kiessling, L. L.; Raines, R. T. *Org. Lett.* 2000, 2, 1939–1941 which is incorporated by reference herein its entirety.

Example 3

Synthesis of a Peptide Phosphinothioester Using a Safety-Catch Resin

Peptide synthesis and activation. 4-Sulfamylbutyryl AM resin (Novabiochem 01-64-0152) was loaded with FmocGlyOH according to the method of Backes and Ellman (Backes, B. J.; Ellman, J. A. *J. Org. Chem.* 1999, 64, 2322–2330). Peptide chain elongation with Glu(tBu) and Cys(Trt) was performed using standard PyBOP/HOBt coupling procedures.

Activation of resin. Approximately 1 g of resin (0.477 mmol of peptide) was preswollen in $CH_2Cl_2$ for 1 h and then drained. Iodoacetonitrile (1.8 mL, 25 mmol), diisopropylethylamine (DIPEA, 1.7 mL, 10 mmol), and 1-methyl-2-pyrrolidinone (NMP, 40 mL) were mixed and filtered through a plug of basic alumina and subsequently added to the resin. The resin was agitated by bubbling Ar(g) at room temperature for 18 h. The resin was then washed with NMP (5×10 mL), DW (5×10 mL), and $CH_2Cl_2$ (5×10 mL). The resin was then immediately used in the subsequent step.

Peptide phosphinothioester release from resin.

(Diphenylphospino)methanethiol (0.88 g, 3.8 mmol) in 20 mL DMF was added to the activated safety-catch resin. The mixture was agitated for 18 h by bubbling Ar(g). The resin was then filtered and washed with DMF (5' 10 mL) and $CH_2Cl_2$ (5' 10 mL). The eluate was collected and solvent was removed under reduced pressure. The residue was purified by chromatography (silica gel, 30% EtOAc in hexanes) to give 285 mg (0.27 mmol) of FmocCys(Trt)Glu(tBu)GlySCH$_2$PPh$_2$ as a white solid. Based on an Fmoc-loading assay for the activated peptide, this represents a 57% yield of the desired peptide phosphinothioester.

Those of ordinary skill in the art will appreciate that methods, reagents, reactants, reaction conditions (e.g., solvents, temperature reaction time) and purification methods other than those specifically disclosed herein can be employed in the practice of this invention without undue experimentation. All art-known functional equivalents of methods, reagents, reactants, reaction conditions and purification methods specifically disclosed or described herein are incorporated by reference herein in their entirety as if each were individually incorporated by reference.

What is claimed is:

1. A method for forming an amide bond which comprises the step of reacting a phosphinothioester with an azide followed by hydrolysis of combined reactants to form an amide bond.

2. The method claim 1 wherein the phosphinothioester is formed by reaction of a activated carboxylic acid derivative with a phosphinothiol.

3. The method of claim 1 wherein the reaction is carried out in the presence of sufficient water to facilitate hydrolysis.

4. The method of claim 1 wherein the reaction is carried out in an aqueous organic medium.

5. The method of claim 4 wherein the reaction is carried out in a mixture of THF and water.

6. The method of claim 2 wherein the phosphinothiol is o-(diphenylphosphino)benzenethiol.

7. The method of claim 2 wherein the phosphinothiol is (diphenylphosphino)methanethiol.

8. The method of claim 1 wherein a peptide is formed.

9. The method of claim 1 wherein a protein is formed.

10. The method of claim 1 wherein the phosphinothioester is a phosphinothioester of an amino acid, peptide or protein.

11. The method of claim 1 wherein the azide is an azide of an amino acid, peptide or protein.

12. The method of claim 1 wherein at least one of the phosphinothioester or the azide is a phosplinothioester or an azide of a β-amino acid.

13. The method of claim 1 wherein at least one of the phosphinothioester or the azide is a phosphinothioester or an azide of an amino acid having an electrophilic side group.

14. The method of claim 1 wherein the phosphinothiol has the formula:

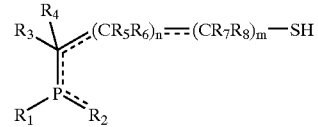

where:

n and m are 0 or integers equal to 1–3, inclusive, and n+m=0–4, inclusive; the dashed line indicates that a double bond may be present or that the bond may be part of an aromatic group and $R_4$, $R_6$ and $R_8$ are not present if there is a double bond between the carbons or the bond is a part of an aromatic ring;

$R_1$ and $R_2$ are groups independently selected from aliphatic, alicyclic, heteroalicyclic, aromatic, or heteroaromatic groups which are optionally substituted, wherein substituents are selected from the group consisting of halides, and OH, OR, COH, COR, COOH, COOR, and N(R')$_2$ groups where R, independent of other R, is an aliphatic, alicyclic, heteroalicyclic, aromatic or heteroaromatic group and each R', independent of other R' are hydrogen, or an aliphatic, alicyclic, heteroalicyclic, aromatic or heteroaromatic groups, R and R' are optionally substituted with substituents as listed for $R_1$ and $R_2$; in $R_1$ and $R_2$, one or more non-neighboring $CH_2$ groups can be replaced with O, S, CO, COO, or CONR'; and $R_3$–$R_8$, independently, are selected from hydrogens, or aliphatic, alicyclic, heteroalicyclic, aromatic or heteroaromatic groups, which can be optionally substituted as listed for $R_1$ and $R_2$, in $R_3$–$R_8$ one or more non-neighboring $CH_2$ groups can be replaced with O, S, CO, COO, or CONR' groups, where R' is defined as for $R_1$ and $R_2$, and where $R_1$ and $R_2$ are optionally covalently linked to form a cyclic group, including a bicyclic group, or two or more of $R_3$–$R_8$ are optionally covalently linked to form a cyclic group, including a bicyclic group.

15. The method of claim 14 wherein the phosphinothiol has the formula:

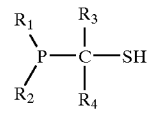

where:

$R_1$ and $R_2$ independently, are groups selected from aliphatic, alicyclic, heteroalicyclic, aromatic, or heteroaromatic groups which are optionally substituted, wherein substituents are selected from the group consisting of halides, and OH, OR, COH, COR, COOH, COOR, and N(R')$_2$ groups, where R, independent of other R, is an aliphatic, alicyclic, heteroalicyclic, aromatic or heteroaromatic group and each R', independent of other R', is a hydrogen, or an aliphatic, alicyclic, heteroalicyclic, aromatic or heteroaromatic group, R and R' are optionally substituted as listed for $R_1$ and $R_2$; and in $R_1$ and $R_2$, one or more non-neighboring CH$_2$ groups can be replaced with O, S, CO, COO, or CONR'; and $R_3$ and $R_4$, independently, are groups selected from hydrogen, or an aliphatic, alicyclic, heteroalicyclic, aromatic or heteroaromatic group, which are optionally substituted as listed for $R_1$ and $R_2$, in $R_3$ and $R_4$ one or more non-neighboring CH$_2$ groups can be replaced with O, S, CO, COO, or CONR' groups where each R' is defined as for $R_1$ and $R_2$, and where $R_1$ and $R_2$ are optionally covalently linked to form a cyclic group, including a bicyclic group, or $R_3$ and $R_4$ are optionally covalently linked to form a cyclic group, including a bicyclic group.

16. The method of claim 15 wherein in the phosphinothiol, $R_3$ and $R_4$ are both hydrogens and $R_1$ and $R_2$ are selected from a phenyl group or a substituted phenyl group.

17. The method of claim 15 wherein the $R_1$ and $R_2$ groups of the phosphinothiol are n-butyl groups.

18. The method of claim 14 wherein the $R_1$ and $R_2$ groups of the phosphinothiol are polyethers.

19. The method of claim 18 wherein at least one of the $R_1$ and $R_2$ groups of the phosphinothiol have the formula:

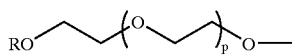

where p is 0 or an integer ranging from 1 to about 10, inclusive, and R is hydrogen or an alkyl group.

20. The method of claim 14 wherein the phosphinothiol has the formula:

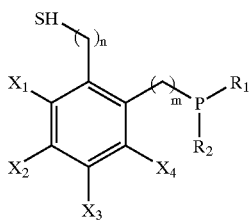

where n and m are 0 or 1 and $X_1$–$X_4$ are substituents on the aromatic group, two of which may be covalently linked to form an alicyclic or aromatic ring, where $X_1$–$X_4$ are hydrogens, halides, optionally substituted aliphatic, alicyclic or aromatic groups, OH or OR, COR, COOH or COOR groups, where R is an optionally substituted aliphatic, alicyclic, aromatic, or N(R')$_2$ group, where each R', independent of other R', is a hydrogen, or an optionally substituted aliphatic, alicyclic or aromatic group.

21. The method of claim 20 wherein $R_1$ and $R_2$ are phenyl or substituted phenyl groups.

22. The method of claim 21 wherein $R_1$ and $R_2$ are phenyl groups substituted with electron donating groups or electron withdrawing groups.

23. A method for synthesis of a peptide or protein wherein at least one of the amide bonds of the peptide or protein is formed by the method of claim 1.

24. The method of claim 23 wherein two peptides formed by conventional solid phase synthesis are ligated by formation of the amide bond.

25. The method of claim 23 wherein two peptides or proteins formed by recombinant DNA expression methods are ligated by formation of the amide bond.

26. The method of claim 23 wherein a peptide or protein formed by conventional solid phase methods is ligated to a peptide or protein formed by recombinant DNA expression methods by formation of the amide bonds.

27. The method of claim 23 wherein a peptide is formed by a sequential series of ligations forming amide bonds between amino acids.

28. A method for labeling a peptide or protein with a reporter molecule which comprises the ligation step of claim 1.

29. A phosphinothiol reagent having the formula:

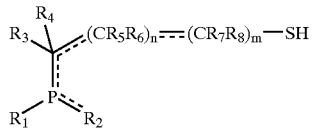

where:

n and m are 0 or integers equal to 1–3, inclusive, and n+m=0–4, inclusive; the dashed line indicates that a double bond may be present or that the bond may be part of an aromatic group, and $R_4$, $R_6$ and $R_8$ are not present if there is a double bond between the carbons or the bond is a part of an aromatic ring;

$R_1$ and $R_2$ are groups independently selected from aliphatic, alicyclic, heteroalicyclic, aromatic, or heteroaromatic groups which are optionally substituted, wherein substituents are selected from the group consisting of halides, and OH, OR, COH, COR, COOH, COOR, and N(R')$_2$ groups, where R, independent of other R, is an aliphatic, alicyclic, heteroalicyclic, aromatic or heteroaromatic group and each R', independent of other R' is a hydrogen, or an aliphatic, alicyclic, heteroalicyclic, aromatic or heteroaromatic group, R and R' are optionally substituted as listed above for $R_1$ and $R_2$; and $R_1$ and $R_2$, one or more non-neighboring CH$_2$ groups can be replaced with O, S, GO, COO, or CONR'; and $R_3$–$R_8$, independently, are selected from hydrogens, or aliphatic, alicyclic, heteroalicyclic, aromatic or heteroaromatic groups which are optionally substituted as listed for $R_1$ and $R_2$, in $R_3$–$R_8$ one or more non-neighboring CH$_2$ groups can be replaced with O, S, CO, COO, or CONR' groups where R' is defined as for $R_1$ and $R_2$, $R_1$ and $R_2$ are optionally covalently linked to form a cyclic group, including a bicyclic group, and two or more of $R_3$–$R_8$ are optionally covalently linked to form a cyclic group, including a bicyclic group wherein the reagent is not o-(diphenylphosphino) benzenethiol.

30. The reagent of claim 29 wherein the phosphinothiol has the formula:

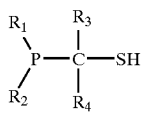

where:
R$_1$ and R$_2$, independently, are groups selected from aliphatic, alicyclic, heteroalicyclic, aromatic, or heteroaromatic groups which are optionally substituted, wherein substituents are selected from the group consisting of halides, and OH, OR, COH, COR, COOH, COOR, and N(R')$_2$ groups, where R, independent of other R, is an aliphatic, alicyclic, heteroalicyclic, aromatic or heteroaromatic group and each R', independent of other R' is a hydrogen, or an aliphatic, alicyclic, heteroalicyclic, aromatic or heteroaromatic group, R and R' are optionally substituted as listed above for R$_1$ and R$_2$; and in R$_1$ and R$_2$, one or more non-neighboring CH$_2$ groups can be replaced with O, S, CO, COO, or CONR'; and R$_3$ and R$_4$, independently, are selected from hydrogens, or aliphatic, alicyclic, heteroalicyclic, aromatic or heteroaromatic groups which are optionally substituted as listed for R$_1$ and R$_2$, in R$_3$ and R$_4$ one or more non-neighboring CH$_2$ groups can be replaced with O, S, CO, COO, or CONR' groups where R' is as defined for R$_1$ and R$_2$, and R$_1$ and R$_2$ $_{or\,R3}$ and R$_4$ are optionally covalently linked to form a cyclic group, including a bicyclic group.

31. The reagent of claim 30 wherein the R$_1$ and R$_2$ groups of the phosphinothiol are n-butyl groups.

32. The reagent of claim 29 wherein the R$_1$ and R$_2$ groups of the phosphinothiol are polyethers.

33. The reagent of claim 29 wherein at least one of the R$_1$ and R$_2$ groups of the phosphinothiol comprise a moiety having the formula:

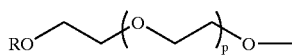

where p is 0 or an integer ranging from 1 to about 10, inclusive, and R is hydrogen or an alkyl group.

34. The reagent of claim 29 wherein the phosphinothiol has the formula:

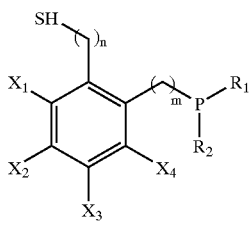

where n and m are 0 are 1 and X$_1$–X$_4$ are substituents on the aromatic group, two of which may be covalently linked to form an alicyclic or aromatic ring, X$_1$–X$_4$ are hydrogens, halides, optionally substituted aliphatic, alicyclic or aromatic groups, OH or OR, COR, COOH or COOR groups, where R is an optionally substituted aliphatic, alicyclic, aromatic, or N(R')$_2$ group, where each R', independent of other R', is a hydrogen, or an optionally substituted aliphatic, alicyclic or aromatic group.

35. The reagent of claim 34 wherein R$_1$ and R$_2$ are phenyl or substituted phenyl groups.

36. The reagent of claim 34 wherein R$_1$ and R$_2$ are phenyl groups substituted with electron donating groups or electron withdrawing groups.

37. The reagent of claim 34 wherein n and m are both 0.

38. The reagent of claim 34 wherein R$_1$ and R$_2$ are both hydrogens.

39. The reagent of claim 34 where R$_1$ and R$_2$ are both phenyl groups.

40. The reagent of claim 34 where R$_1$ and R$_2$ are both n-butyl groups.

41. The reagent of claim 29 which is (diphenylphosphino)methanethiol.

42. A kit for forming an amide bond between an activated carboxylic acid derivative and an azide which comprises one or more reagents for generating an azide and one or more of the phosphinothiol reagents of claim 29.

43. A kit for synthesis of peptides or proteins which comprises one or more of the phosphinothiol reagents of claim 29 and one or more protective agents for amino acid side chains.

44. The kit of claim 43 further comprising a resin for solid phase synthesis.

45. The kit of claim 44 wherein the resin is a safety-catch resin.

46. The kit of claim 43 further comprising a reagent for generating azido peptides.

47. The kit of claim 43 further comprising a reagent for generating thioesters.

48. A kit of claim 42 further comprising one or more solvents for conducting amide bond formation and optionally containing instructions for carrying out amide bond formation.

49. The method of claim 1 wherein the phosphinothioester is a phosphinothioester of a lipid.

50. The method of claim 49 wherein the azide is an azido peptide or an azido protein.

51. The method of claim 1 wherein the azide is a nucleoside azide.

52. The method or claim 51 wherein the phosphinothioester is a phosphinothioester of a peptide or an azido protein.

53. The method of claim 1 wherein the amide bond ligates a saccharide to a peptide.

54. The method of claim 1 wherein the amide bond ligates a lipid to a peptide.

55. The method of claim 1 wherein the amide bond ligates a nucleoside to a peptide.

56. The method of claim 1 wherein the amide bond ligates a nucleic acid to a peptide.

57. The reagent of claim 30 wherein R$_3$ and R$_4$ are both hydrogens.

58. The reagent of claim 57 wherein R$_1$ and R$_2$ are phenyl groups or substituted phenyl groups.

* * * * *

UNITED STATES PATENT AND TRADEMARK OFFICE
CERTIFICATE OF CORRECTION

| | | |
|---|---|---|
| PATENT NO. | : 6,972,320 B2 | Page 1 of 1 |
| APPLICATION NO. | : 10/276515 | |
| DATED | : December 6, 2005 | |
| INVENTOR(S) | : Ronald T. Raines et al. | |

It is certified that error appears in the above-identified patent and that said Letters Patent is hereby corrected as shown below:

In the Specification

Column 1, Lines 16-19:
Delete the phrase:
"This invention was made with United States government support awarded by the National Institute of Health No. GM 44783. The United States government has certain rights in this invention."
And replace with:
--This invention was made with government support under GM044783 awarded by the National Institutes of Health. The government has certain rights in the invention.--.

Signed and Sealed this
First Day of December, 2020

Andrei Iancu
*Director of the United States Patent and Trademark Office*